US009389214B2

(12) United States Patent
Adamchuk et al.

(10) Patent No.: US 9,389,214 B2
(45) Date of Patent: Jul. 12, 2016

(54) SOIL ANALYSIS APPARATUS, METHOD, AND SYSTEM HAVING A DISPLACEABLE BLADE ASSEMBLY AND SENSOR

(71) Applicant: The Royal Institution for the Advancement of Learning/McGill University, Montreal (CA)

(72) Inventors: Viacheslav Adamchuk, Ste-Anne-de-Bellevue (CA); Nandkishor Dhawale, Ste-Anne-de-Bellevue (CA); Frédéric René-Laforest, Montreal (CA); Shiv Prasher, Baie d'Urfé (CA); Antoine Pouliot, Ste-Anne-de-Bellevue (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 122 days.

(21) Appl. No.: 14/494,719

(22) Filed: Sep. 24, 2014

(65) Prior Publication Data
US 2015/0087072 A1 Mar. 26, 2015

Related U.S. Application Data

(60) Provisional application No. 61/881,747, filed on Sep. 24, 2013.

(51) Int. Cl.
*G01N 33/24* (2006.01)
*G01N 27/414* (2006.01)

(52) U.S. Cl.
CPC ............. *G01N 33/24* (2013.01); *G01N 27/414* (2013.01); *G01N 2033/245* (2013.01)

(58) Field of Classification Search
CPC ..... G01N 27/414; G01N 33/24; G01N 2033/245
USPC ...................................... 422/68.1; 436/25, 28
See application file for complete search history.

(56) References Cited

U.S. PATENT DOCUMENTS

| 4,411,160 A | 10/1983 | Lutenegger et al. |
| 5,044,756 A | 9/1991 | Gaultney et al. |

(Continued)

FOREIGN PATENT DOCUMENTS

| WO | 9853312 A1 | 11/1998 |
| WO | 2012094116 A1 | 7/2012 |

OTHER PUBLICATIONS

Mouazen, A. M. et al, Soil & Tillage Research 2005, 80, 171-183.*

(Continued)

*Primary Examiner* — Arlen Soderquist
(74) *Attorney, Agent, or Firm* — Bereskin & Parr LLP/S.E.N.C.R.L., s.r.l.

(57) ABSTRACT

A soil analysis apparatus includes at least one sensor element for measuring a property of the soil; a blade assembly having at least one blade and being displaceable between a raised position and an excavation position, the at least one blade being operable to excavate the soil at a test location when the blade assembly is in the excavation position, the blade assembly being further operable to enter a sensor permitting configuration; and a first actuator operable to displace the at least one sensor element between an initial position and a sensing position along a sensor displacement path, the sensor element being proximate the soil at the test location when in the sensing position.

23 Claims, 21 Drawing Sheets

(56) References Cited

U.S. PATENT DOCUMENTS

| | | | |
|---|---|---|---|
| 5,128,882 A | | 7/1992 | Cooper et al. |
| 5,358,057 A | | 10/1994 | Peters et al. |
| 5,375,663 A | | 12/1994 | Teach |
| 5,461,229 A | * | 10/1995 | Sauter .................... G01N 21/71 250/253 |
| 5,542,781 A | | 8/1996 | Yemington et al. |
| 5,663,649 A | | 9/1997 | Topp et al. |
| 5,673,637 A | * | 10/1997 | Colburn, Jr. ......... A01B 79/005 111/118 |
| 5,847,825 A | | 12/1998 | Alexander |
| 5,887,491 A | * | 3/1999 | Monson ............... A01B 79/005 250/253 |
| 5,902,939 A | | 5/1999 | Ballard et al. |
| 6,356,830 B1 | | 3/2002 | Adamchuck et al. |
| 6,853,937 B2 | | 2/2005 | Shibusawa et al. |
| 7,040,146 B2 | | 5/2006 | Mackenzie et al. |
| 2003/0016029 A1 | * | 1/2003 | Schuler .................. A01B 35/32 324/643 |
| 2005/0172733 A1 | | 8/2005 | Drummond et al. |
| 2006/0158652 A1 | | 7/2006 | Rooney et al. |
| 2009/0107725 A1 | | 4/2009 | Christy et al. |
| 2009/0112475 A1 | * | 4/2009 | Christy ................ A01B 79/005 702/5 |
| 2010/0034048 A1 | | 2/2010 | Jagle |
| 2011/0102798 A1 | * | 5/2011 | Holland ............... A01B 79/005 356/445 |
| 2011/0106451 A1 | | 5/2011 | Christy et al. |
| 2013/0104785 A1 | * | 5/2013 | Achen .................... A01C 5/062 111/157 |
| 2014/0034339 A1 | | 2/2014 | Sauder et al. |
| 2014/0041263 A1 | | 2/2014 | Bockman |
| 2014/0048001 A1 | | 2/2014 | Bassett |
| 2014/0048295 A1 | | 2/2014 | Bassett |
| 2014/0048296 A1 | | 2/2014 | Bassett |
| 2014/0251032 A1 | | 9/2014 | Scheiderer et al. |

OTHER PUBLICATIONS

Adamchuk, V. I. et al, Computers and Electronics in Agriculture 2005, 48, 272-294.*

Minzan, L., SPIE 2005, 5881, 588101, 11 pages.*

Adamchuk, V. I. et al, in "Proximal Soil Sensing, Progress in Soil Science 1" 2010, R.A. Viscarra Rossel et al. (eds.), 15-28.*

Adamchuk, V.I., Morgan, M.T., and Ess, D.R. 1999. An automated sampling system for measuring soil pH. Transactions of ASAE, 42, 885-891.

Adamchuk, V.I., Hummel, J.W., Morgan, M.T., and Upadhyaya, S.K. 2004. On-the-go soil sensors for precision agriculture. Computer and Electronics in Agriculture, 44, 71-91.

Adamchuk, V.I. and Lund, E.D. 2008. On-the-go mapping of soil pH using antimony electrodes. Paper No. 08-3995. St. Joseph, Michigan: ASABE.

Adamchuk, V.I., Viscarra Rossel, R.A., Sudduth, K.A., and Schulze Lammers, P. 2011. Sensor fusion for precision agriculture. In: Sensor Fusion—Foundation and Applications, Chapter 2, 27-40, C. Thomas, ed. InTech, Rijeka, Croatia.

Adsett, J.F. and Zoerb, G.C. 1991. Automated field monitoring of soil nitrate levels. In: Automated Agriculture for the 21st Century, Proceedings of the 1991 Symposium, 326-335. ASABE, St. Joseph, Michigan, USA.

Artigas, J., Beltran, A., Jimenez, C., Baldi, A., Mas, R., Dominguez, C., and Alonso, J. 2001. Application of ion sensitive field-effect transistor based sensors to soil analysis. Computer and Electronics in Agriculture, 31, 281-293.

Birrell, S.J., and Hummel, J.W. 2001. Real-time multi ISFET/FIA soil analysis system with automatic sample extraction. Computer and Electronics in Agriculture, 32, 45-67.

Hummel, J.W., Gaultney, L.D, and Sudduth, K.A. 1996. Soil property sensing for site-specific crop management. Computers and Electronics in Agriculture, 14, 121-136.

Kim, H.J., Hummel, J.W., Sudduth, K.A., and Birrell, S.J. 2007. Evaluation of phosphate ion-selective membranes and cobalt-based electrodes for soil nutrient sensing. Transactions of ASABE, 50, 415-425.

Kim, H.J., Sudduth, K.A., and Hummel, J.W. 2009. Soil macronutrient sensing for precision agriculture. Journal of Environmental Monitoring, 11, 1810-1824.

Shibusawa, S. 2006. Soil sensors for precision agriculture. In: Handbook of Precision Agriculture. Principles and Applications, A. Srinivasan, ed., 57-90. Food Products Press, New York, New York, USA.

Sibley, K.J., Astatkie, T., Brewster, G., Struik, P.C., Adsett, J.F., and Pruski, K. 2009. Field-scale validation of an automated soil nitrate extraction and measurement system. Precision Agriculture, 10, 162-174.

Sudduth, K.A., Hummel, J.W., and Birrell, S.J. 1997. Sensors for site-specific management. In: The State of Site-Specific Management for Agriculture, F.T. Pierce and E.J. Sadler, eds., 183-210, ASA-CSSA-SSSA, Madison, Wisconsin, USA.

Viscarra Rossel, R.A. and McBratney, A.B. 1997. Preliminary experiments towards the evaluation of a suitable soil sensor for continuous 'on-the-go' field pH measurements. In: Precision Agriculture '97, vol. II: Technology, IT and Management, J.V. Stafford, ed., 493-502. Bios Scientific Publishers Ltd, Oxford, UK.

Viscarra Rossel, R.A., Gilbertsson, M., Thyle'n, L., Hansen, O., McVey, S., and McBratney, A.B. 2005. Field measurements of soil pH and lime requirement using an on-the-go soil pH and lime requirement measurement system. In: Precision Agriculture '05, J.V. Stafford, ed., Wageninen Academic Publishers, Wageninen, The Netherlands.

Viscarra Rossel, R.A., Adamchuk, V.I., Sudduth, K.A., McKenzie, N.J., and Lobsey, C. 2011. Proximal soil sensing: an effective approach for soil measurements in space and time, Chapter 5. Advances in Agronomy, 113, 237 283.

* cited by examiner

SOIL ANALYSIS APPARATUS, METHOD, AND SYSTEM HAVING A DISPLACEABLE BLADE ASSEMBLY AND SENSOR

CROSS-REFERENCES TO RELATED APPLICATIONS

The present application claims priority from U.S. provisional patent application No. 61/881,747, filed Sep. 24, 2013 and entitled "ON-THE-SPOT SOIL ANALYZER", the disclosure of which is hereby incorporated by reference in its entirety.

FIELD

The application relates to a soil analyzer, and more particularly to an apparatus, system, and method for completing an automated analysis of soil at a test location.

INTRODUCTION

The rapid rise in demand for crop quantity/quality and the growing concern of non-point pollution caused by modern farming practices, challenge the efficiency and environmental safety of agricultural production systems. Agricultural inputs vary across the landscape due to naturally and man-made differences in key productivity factors such as water and nutrient supply. Crop management practices have to be adapted to locally defined needs.

Traditionally, differences in physical, chemical and biological soil attributes have been detected through soil sampling and laboratory analysis. The high cost of sampling and analysis limits the number of samples and does not allow accurate characterization of the landscape variability.

The present disclosure refers to a number of documents, the contents of which are herein incorporated by reference in their entirety.

SUMMARY

According to one aspect, the present disclosure relates to a soil analysis apparatus comprising: at least one sensor element for measuring a property of a soil; a blade assembly having at least one blade and being displaceable between a raised position and an excavation position, the at least one blade being operable to excavate the soil at a test location when the blade assembly is in the excavation position, the blade assembly being further operable to enter at least a sensor element permitting configuration; and a first actuator operable to displace the at least one sensor element between an initial position and a sensing position along a sensor displacement path when the blade assembly is in the sensor permitting configuration, the sensor element being proximate to the soil at the test location when in the sensing position.

According to another aspect, the present disclosure relates to a method for sensing or measuring at least one soil property at a test location, the method comprising: displacing a blade assembly and rotating at least one blade of the blade assembly to excavate soil material at the test location; displacing the blade assembly to a raised position away from the test location; displacing at least one sensor element into a sensing position; and sensing or measuring at least one soil property at the test location.

According to another aspect, the present disclosure relates to a method for sensing or measuring at least one soil property at a test location, the method comprising: displacing a blade assembly and rotating at least one blade of the blade assembly to excavate soil material at the test location; detecting a predetermined rotational position of the at least one blade; displacing at least one sensor element into a sensing position along a sensor displacement path; and sensing or measuring at least one soil property at the test location.

The foregoing and other advantages and features of the present disclosure will become more apparent upon reading of the following non-restrictive description of illustrative embodiments thereof, given by way of example only with reference to the accompanying drawings/figures.

DRAWINGS

For a better understanding of the embodiments described herein and to show more clearly how they may be carried into effect, reference will now be made, by way of example only, to the accompanying drawings which show at least one exemplary embodiment, and in which.

DESCRIPTION OF VARIOUS EMBODIMENTS

Figure 1:
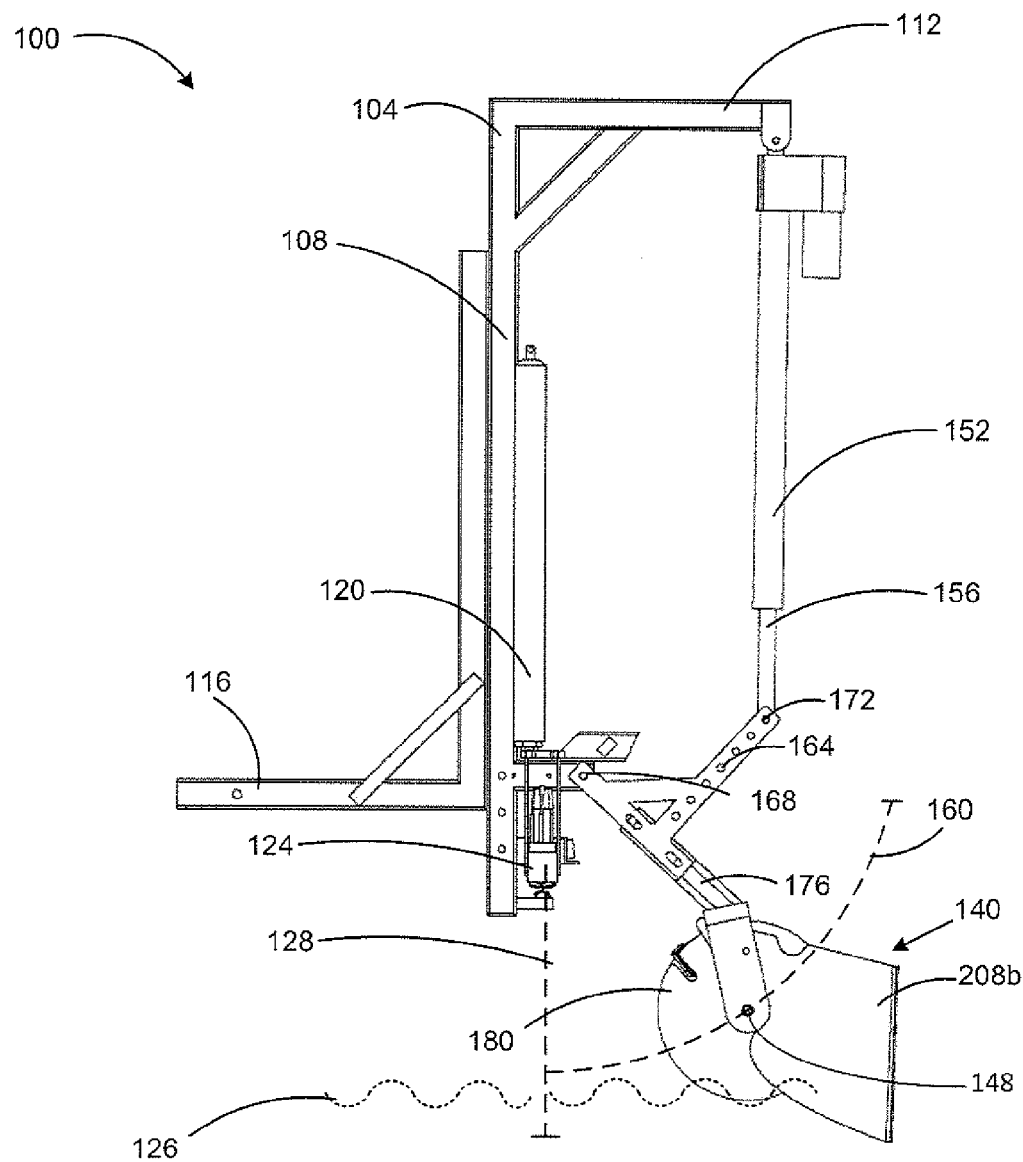
FIG. 1 is a side elevation view of an example soil analysis apparatus, showing a blade assembly being displaced from a raised position towards an excavation position, and a sensor element in an initial position.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any invention disclosed in an apparatus or process described below and for which an exclusive right is not granted by issuance of this patent application may be the subject matter of another protective instrument, for example, a continuing patent application, and the applicants, inventors or owners do not intend to abandon, disclaim or dedicate to the public any such invention by its disclosure in this document.

The word "a" or "an" when used in conjunction with the term "comprising" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±1% of the modified term if this deviation would not negate the meaning of the word it modifies.

The terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices are directly connected to one another or connected to one another through one or more intermediate elements or devices via an electrical element, electrical signal or a mechanical element depending on the particular context.

Figure 2:
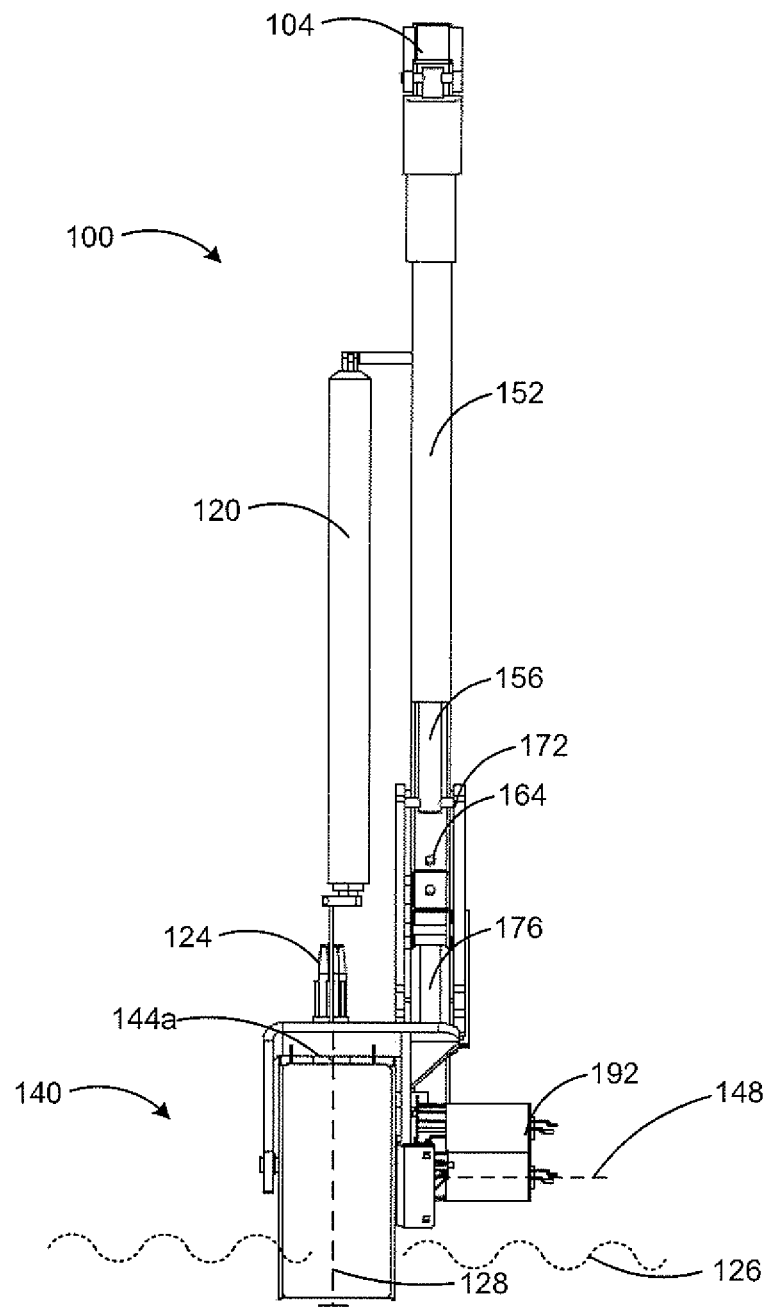
FIG. 2 is a rear elevation view of the soil analysis apparatus of FIG. 1.
Figure 3:
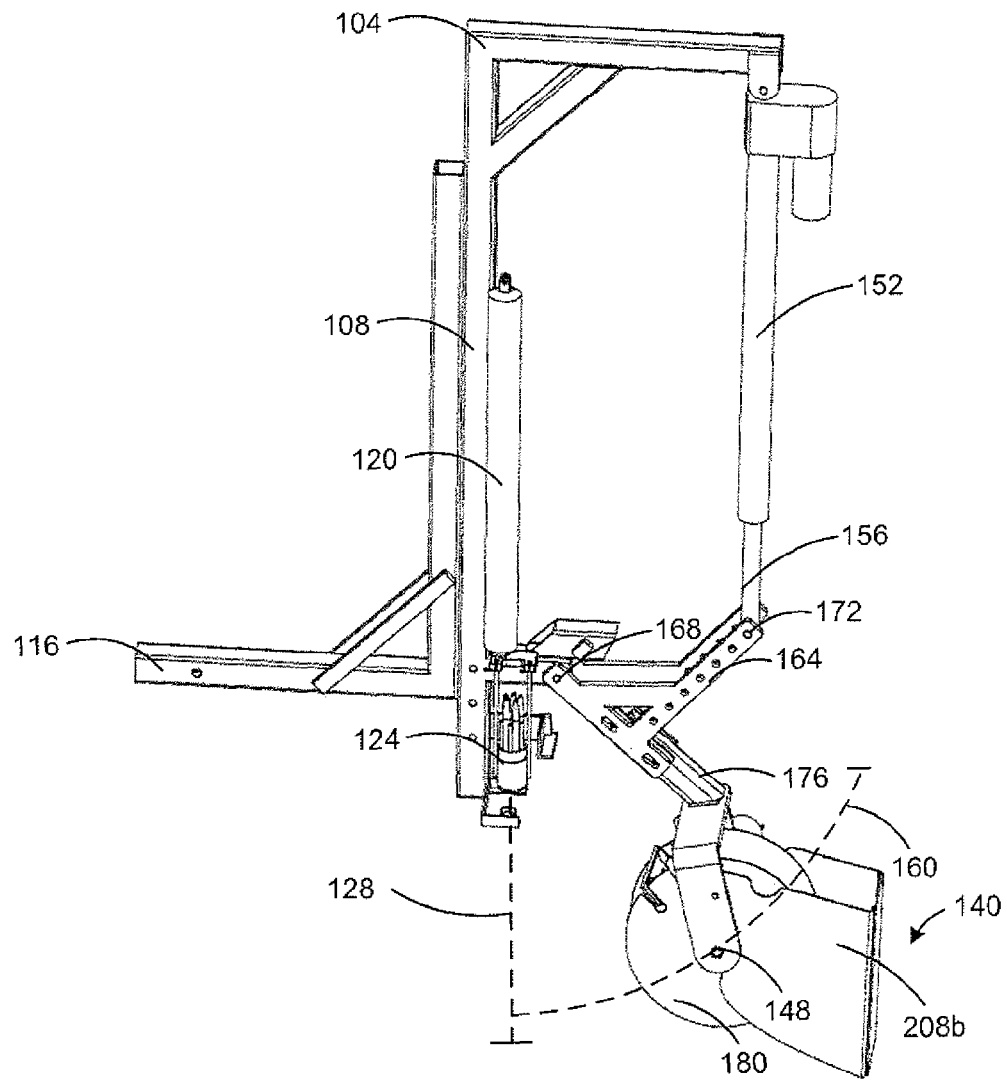
FIG. 3 is a perspective view of the soil analysis apparatus of FIG. 1.

Referring now to FIGS. 1, 2 and 3, therein illustrated are a side elevation view, rear elevation view and perspective view respectively of an example soil analysis apparatus 100. The soil analysis apparatus 100 has a frame 104, which may have an elongated member 108 and a first transverse member 112 extending transversely from the elongated member 108. A second transverse member 116 may further extend transversely from the elongated member 108. The second transverse member 116 may have a connector (not shown) adapted to cooperate with a hitch of a vehicle, thereby allowing the soil analysis apparatus 100 to be mounted onto a vehicle.

In the example shown, the soil analysis apparatus 100 has a first actuator 120 that is coupled to the frame 104. The first actuator 120 may be coupled to the elongated member 108 of the frame 104. The first actuator 120 can be any actuator providing for sensor displacement allowing engagement between the sensor (described below) and the tested soil. In the example shown, the first actuator 120 is a linear actuator, and the direction of the actuation of the actuator 120 is substantially parallel to the length of the elongated member 108. The first actuator 120 may be an electrical actuator, and may include a 12 V DC high-speed linear motor.

At least one sensor element 124 may be coupled to the first actuator 120. The sensor element 124 may be configured to analyze or examine at least one property of soil material to be analyzed. The sensor element 124 may be any sensor element that analyzes or examines a property of soil, such as one that requires contact or proximal placement to the soil. Non-limiting examples of sensor elements include ion-selective electrodes or ion-selective field effect transistors (pH, potassium, nitrate, sodium, etc.), various optical sensing systems, time-domain or frequency domain reflectrometry sensors, or any other devices suitable or adaptable for in situ measurements of soil.

In some examples, the sensor element 124 is a sensor assembly comprising at least one sensor.

In some examples, the at least one sensor element 124 may include a flat surface single junction pH electrode and an antimony pH electrode for measuring soil acidity. A nitrate ISE may be used to measure soil nitrate ion activity. Other electrodes or combination of electrodes may also be provided in the at least one sensor element 124.

In some examples, data acquisition cards may be used to receive measurements made by the electrodes of the at least one sensor element 124. For example, inline unity gain pre-amplifiers may be provided to match the impedance between electrodes and the data acquisition card interface. For more accurate measurements, independent data acquisition cards may be used for each sensor electrode. For example, the pre-amplifiers may be powered independently using their own battery packs.

The first actuator 120 may be operable to displace the at least one sensor element 124 between at least an initial position (shown in FIGS. 1 to 3, 7, 10, and 11D) and a sensing position (shown in FIGS. 8, 9, 11A, 11B, and 11C). The at least one sensor element 124 may be displaced between the initial position and the sensing position as a rod portion 125

(see FIGS. 8 and 11A) of the first actuator 120 is actuated. For example, the initial position of the at least one sensor element 124 may correspond to a retracted position of the rod portion 125 of the first actuator 120, whereas the sensing position of the at least one sensor element 124 may correspond to an extended position of the rod portion 125 of the first actuator 120. The initial position may include a range of positions in which the rod portion 125 of the first actuator 120 is at or near its retracted position. In some particular examples, the initial position is a position in which the sensor element 124 is positioned suitable for system transportation and/or sensor cleaning. The sensing position may correspond to a range of positions in which the rod portion 125 of the first actuator 120 is in an extended position sufficient for the sensor element 124 to sense the soil.

In some examples, when the soil analysis apparatus 100 is mounted onto a vehicle that is positioned on a soil surface 126, the rod portion 125 of the first actuator 120 is oriented towards the soil surface 126. When the rod portion 125 of the first actuator 120 is actuated towards its retracted position, the sensor element 124 is moved away from the soil surface 126, towards its initial position; when the rod portion 125 of the first actuator 120 is actuated towards its extended position, the sensor element 124 is moved towards the soil surface 126, towards its sensing position. The soil surface 126 typically comprises a layer of soil to be analyzed.

Displacement of the at least one sensor element 124 between the initial position and the sensing position defines a sensor displacement path 128. For example, where the first actuator 120 is a linear actuator, the sensor displacement path 128 is linear. In some examples, extending the rod portion 125 of the first actuator 120 into a sensing configuration results in the at least one sensor element 124 at least intersecting a plane defined by the soil surface 126. When the at least one sensor element 124 is proximate the soil surface 126 or is contacting the soil surface 126, at least one property of the soil can be analyze/measured.

In other examples, the sensor displacement path 128 may be non-linear. For example, the first actuator 120 may extend non-linearly. Alternatively, the sensor element 124 may be pivotally mounted in such a way that linear actuation of the first actuator 120 causes the sensor element 124 to be displaced along a non-linear displacement path 128.

In some examples, the sensor element 124 is coupled to the rod portion 125 of the first actuator 120 via one or more shock absorbers. For example, the sensor element 124 may be mounted to the rod portion 125 using one or more springs. Accordingly, firm but gentle contact of the sensor element 124 with the soil surface 126 can be made as the sensor element 124 is displaced to its sensing position.

Continuing to refer to FIGS. 1 to 3, in the example shown, the soil analysis apparatus 100 further includes a blade assembly 140. The blade assembly 140 can be coupled to the frame 104. The blade assembly 140 may include at least one blade. In some examples, the blade assembly 140 includes at least two blades. In the example shown, the blade assembly 140 includes two blades 144a and 144b (shown in FIGS. 4 and 6B).

In the example shown, the blades 144a, 144b are rotatable about an axis 148. The axis of rotation 148 is substantially perpendicular to the sensor displacement path 128, and substantially parallel to the soil surface 126. The at least one blade may optionally be formed of hardened steel.

In the example shown, the soil analysis apparatus 100 further includes a second actuator 152 that is coupled to the frame 104. As illustrated in FIGS. 1 and 3, the second actuator 152 is coupled to the first transverse member 112 of frame 104. The second actuator 152 may facilitate movement of the blade assembly 140 between the raised position and the excavation position, towards and away from the soil.

In the example shown, the second actuator 152 is a linear actuator, and is an electrical actuator. In some particular examples, the electrical actuator includes a 12 V DC high-speed linear motor.

The blade assembly 140 is coupled to a rod portion 156 of the second actuator 152. The second actuator 152 is operable to displace the blade assembly 140 between a raised position (shown in FIGS. 8, 9, and 10) and an excavation position (shown in FIGS. 7, 11A, 11B, and 11D). The raised position may include a range of positions in which the blade assembly 140 is above the soil surface 126. The excavation position may include a range of positions in which the blade assembly 140 at least partially contacts the soil surface 126.

Displacement of the blade assembly 140 between its raised position and its excavation position defines a blade assembly displacement path 160 that is followed by the blade assembly 140. In some examples, when in one or more positions along the blade assembly displacement path 160, the blade assembly 140 may occupy space that can also be occupied by the at least one sensor 124, when the sensor 124 is in one or more positions along the sensor displacement path 128. That is, the blade assembly displacement path 160 and the sensor displacement path 128 may intersect at at least one point. For example, when the blade assembly 140 is displaced to the excavation position, the blade assembly 140 occupies a portion of the sensor displacement path 128, as shown in FIG. 7, 11A, 11B, 11C, and 11D. This portion of the sensor displacement path 128 corresponds to the location of the sensor 124 when in the sensing position.

Furthermore, when in other positions along the blade displacement path 160, the blade assembly 140 occupies a space that is remote of the sensor displacement path 128. That is, when in at least a second position along the blade assembly displacement path 160, the blade assembly 140 occupies a space that will not be occupied by the at least one sensor 104 at any point along the sensor displacement path 128. For example, when displaced to the raised position, the blade assembly 140 occupies a space that is remote of the sensor displacement path 128, as shown in FIGS. 1 to 3, 8, 9, and 10.

Furthermore, in at least a second position along the sensor displacement path 108, the at least one sensor 124 occupies a space that is remote of the blade assembly path 160. That is, in at least the second position along the sensor displacement path 128, the at least one sensor 104 occupies a space that will not be occupied by the blade assembly 140 at any position along the blade assembly displacement path 160. For example, when displaced to the initial position, as shown in FIGS. 1 to 3, 7, and 10, the at least one sensor 124 occupies a space that is remote of the blade assembly displacement path 160.

In the example shown, the blade assembly 140 is pivotally mounted to frame 104. As shown in FIGS. 1 and 3, a pivoting member 164 is pivotally mounted at a first point 168 to frame 104 and coupled at a second point 172 to the rod portion 156 of the second actuator 152. The pivoting member 164 is further coupled at a third point 176 to a bracket portion 178 of the blade assembly 140. As the rod portion 156 of the second actuator 152 is extended or retracted, the pivoting member 164 pivots about the first attachment point 168, thereby displacing the blade assembly 140 along the blade assembly displacement path 160. In some examples, the second actuator 152 may be pivotally attached to the first transverse member 112 of the frame 104.

During a soil excavation operation, the at least one blade of the blade assembly 140 may be rotated while the blade assembly 140 is displaced from its raised position towards the excavation position. As the blade assembly 140 is displaced towards its excavation position, the blade assembly 140 will come into contact with a top surface of an underlying soil surface 126, such as the topsoil of a test location. Rotation of the at least one blade of the blade assembly 140 causes an excavation edge of the at least one blade to contact the top surface and remove material therefrom. The rotation of the at least one blade about the axis 148 causes a digging action of the at least one blade, thereby removing topsoil of the test location. For example, and as illustrated in FIGS. 1 to 3, the blade assembly 140 is in a soil excavating position, between its excavation position and its raised position. In the soil excavating position, the blade assembly 140 contacts a top surface of the soil surface 126. As soil material is removed, the blade assembly 140 continues along its blade assembly displacement path 160 to reach its excavation position.

As the blade assembly 140 is further displaced from the position in contact with the top surface of the underlying soil surface 126 towards its excavation position, a greater portion of the blade assembly 140 will be lowered beneath the top surface of the underlying soil surface 126, thereby removing more material from the soil surface 126, thereby digging a larger hole at the test location. The depth of hole can be controlled depending on the sensing application. In some examples, the depth of the hole is controlled by the second actuator 152, and may for example be limited by the position of the motor 192.

Figure 4:
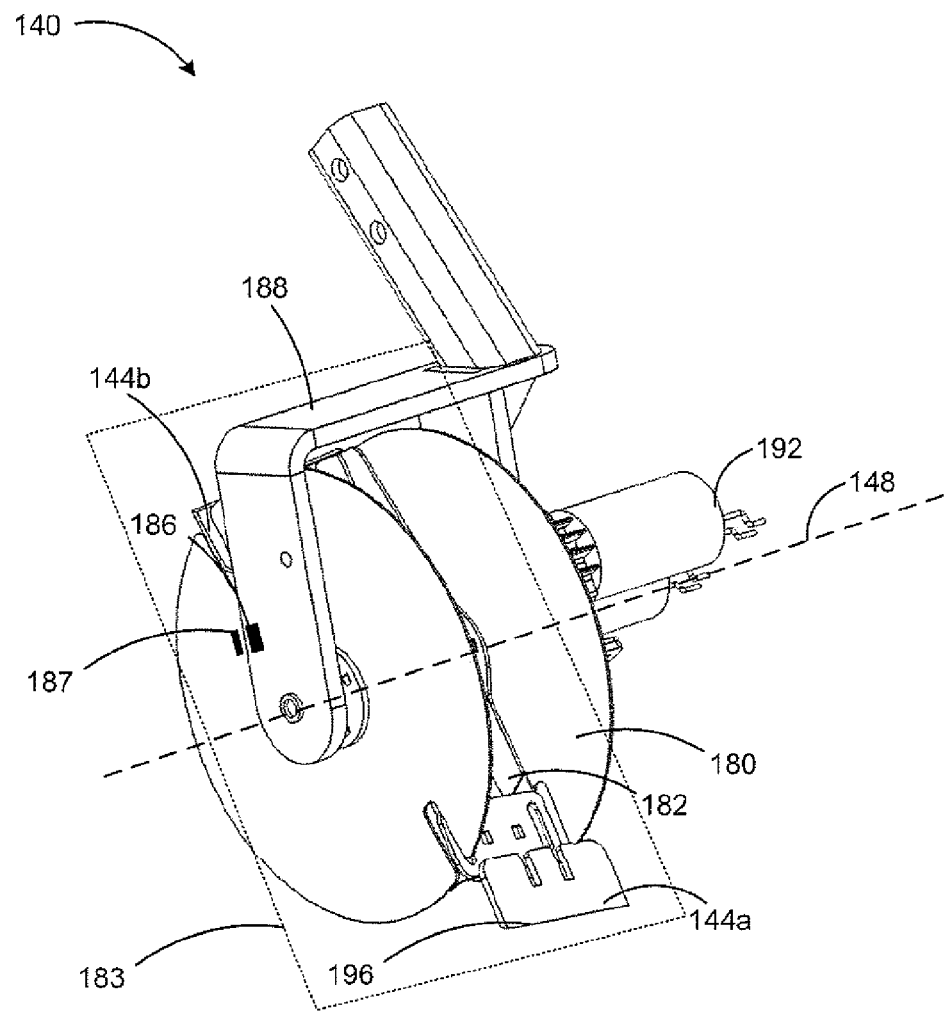
FIG. 4 is an enlarged perspective view of the blade assembly of the soil analysis apparatus of FIG. 1, with a guard member removed therefrom.

Referring now to FIG. 4, therein illustrated is an example blade assembly 140. In the example shown, the blade assembly 140 includes at least one disk member 180 and a support member 188. The at least one disk member 180 may be formed of aluminum. The at least one disk member 180 is rotatably mounted at its center to the support member 180 and rotates about the attachment point. The center of the disk member 180 defines the axis of rotation 148 of the disk member 180 and the blades 144a, 144b.

In the example shown, the blade assembly 140 has an interior opening 182 that is partly defined and bounded by the two rotatable blades 144a, 144b. In the example shown, the interior opening 182 is generally planar, shown schematically at plane 183 in FIG. 4. Plane 183 is generally parallel with the blades 144a, 144b. As the blades 144a, 144b are rotated, the opening 182 and the plane 183 are also rotated. When the blade assembly 140 occupies a space that can also be occupied by the at least one sensor element 124 (e.g. when the blade is in the excavation position), the blades 144a, 144b have at least one rotational (i.e. angular) position in which the interior opening 182 is aligned with the sensor displacement path 128. In this position, the plane 183 is generally transverse to the sensor displacement path 128. This position permits displacement of the at least one sensor element 124 through the interior opening 182. The at least one sensor element 124 can be displaced through the interior opening 182 between its initial position and its sensing position.

The interior opening 182 can be appropriately sized so that when the at least one rotatable blade is in at least one predetermined rotational position, the at least one sensor element 124 can be displaced through the interior opening 182. The at least one predetermined rotational position can include a range of rotational positions allowing passage of the at least one sensor element 124 through the interior opening 182. When the blades 144a, 144b are in the predetermined rotational position, the interior opening may be aligned with the test location of the ground being excavated.

In some examples, the support member 188 is a fork including two attachment points for a disk member 180. At least one motor 192 can be further coupled to the at least one disk member 180 to provide a rotational force thereto. In some examples, more than one motor (ex: two DC motors) may be provided for greater torque. At least one blade is mounted to a circumferential portion of the disc member 180. An excavating edge 196, corresponding to the edge contacting the topsoil of the ground during excavation, is oriented radially to the disk member 180. As the at least one circular disk member 180 is rotated about axis 148, the at least one blade is also rotated thereabout.

In the example shown, two disc members 180 are mounted to the support member 188 and are spaced apart from one another. Each of the two disc members 180 are rotatably mounted to a member of the support member 188. The centers of the two disc members 180 are aligned to define the axis of rotation 148. A first blade 144a and a second blade 144b are mounted to the circumferential portions of the disk members 180 (see also FIG. 6A). The first blade 144a and the second blade 144b may in some examples be spaced by 180° about the circumferential portion of the disk members 180, and the width of each blade 144a, 144b may be oriented at an angle with respect to a radial direction of the blade assembly 140, to improve the structural integrity of the blades 144a, 144b during excavation.

In some examples, the excavating edge 196 of each of the first and second blades 144a and 144b respectively are oriented radially to the disc members 180 and away from each other. As the two disc members 180 are rotated about axis of rotation 148, each blade alternately contacts the top surface of the soil surface 126 to excavate soil therefrom.

According to the example illustrated in FIG. 4, the two circular disc members 180 and the interior edges of the first blade 144a and the second blade 144b define the interior opening 182.

The blade assembly 140 may further include a detector for detecting a rotational position of the at least one rotatable blade. The detector may further output a signal indicating that the at least one rotatable blade is in a predetermined rotational position that permits displacement of the at least one sensor element 124 through the interior opening 182.

In some examples, the detector is a reed switch. A first reed 186 of the reed switch may be located on a non-rotating portion of the blade assembly 140 and a second reed 187 of the reed switch may be located on a rotating portion of the blade assembly 140. The locations of the first and second reeds 186 and 187 may be selected such that alignment of the two reeds indicates that the at least one rotatable blade is in a predetermined rotational position that permits displacement of the at least one sensor element 124 through the interior opening. In some examples, the first reed 186 is located on one of the members of the support member 188, whereas the second reed 187 is located on one of the two circular disk members 180.

In an alternative example, the detector is a potentiometer. For example, the potentiometer may be a continuous turn potentiometer. The potentiometer may include a wiper that turns about a circumferential resistive material strip. The wiper may further turn with the rotation of the at least one rotatable blade. The value of the resistance of the potentiometer will vary depending on the position of the wiper about the resistive material strip. This value can then be used to indicate a position of the at least one rotatable blade. For example, the value of the resistance of the potentiometer can be determined using an ohmmeter or by measuring the output voltage across the potentiometer in a voltage divider having a known voltage applied thereto.

Figure 5:
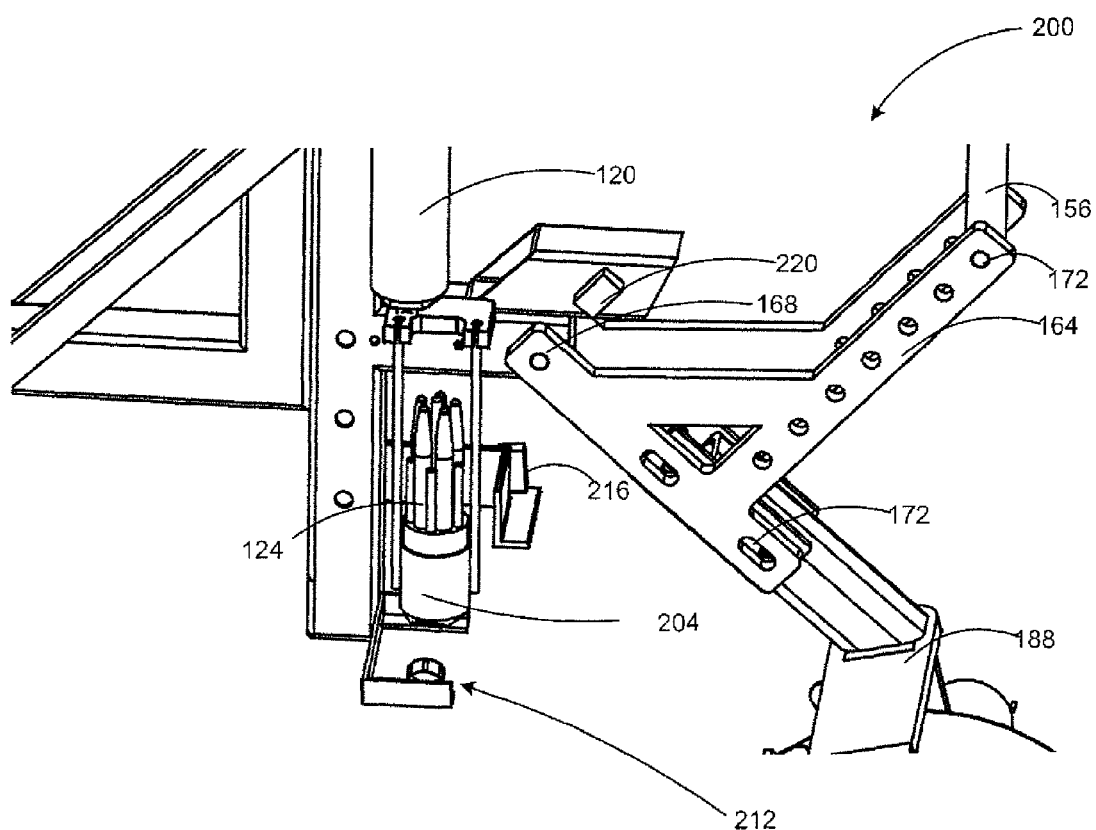
FIG. 5 is an enlarged perspective view of the sensor housing portion of the soil analysis apparatus of FIG. 1.

Referring now to FIG. 5, therein illustrated is a perspective view of the at least one sensor element 124 in an initial position. In the example shown, a plurality of sensor elements can be positioned within a housing 204 that is coupled to the first actuator 120.

In the example shown, the soil analysis apparatus 100 includes a guard member. A first example of a guard member 208a is shown in FIGS. 8, 9, 11B, 11C, and 11D. A second example of a guard member 208b is shown in FIGS. 1 to 3, 6A, 6B, 7 to 10, 11A, 11B, 11C, and 11D.

Figure 11A:
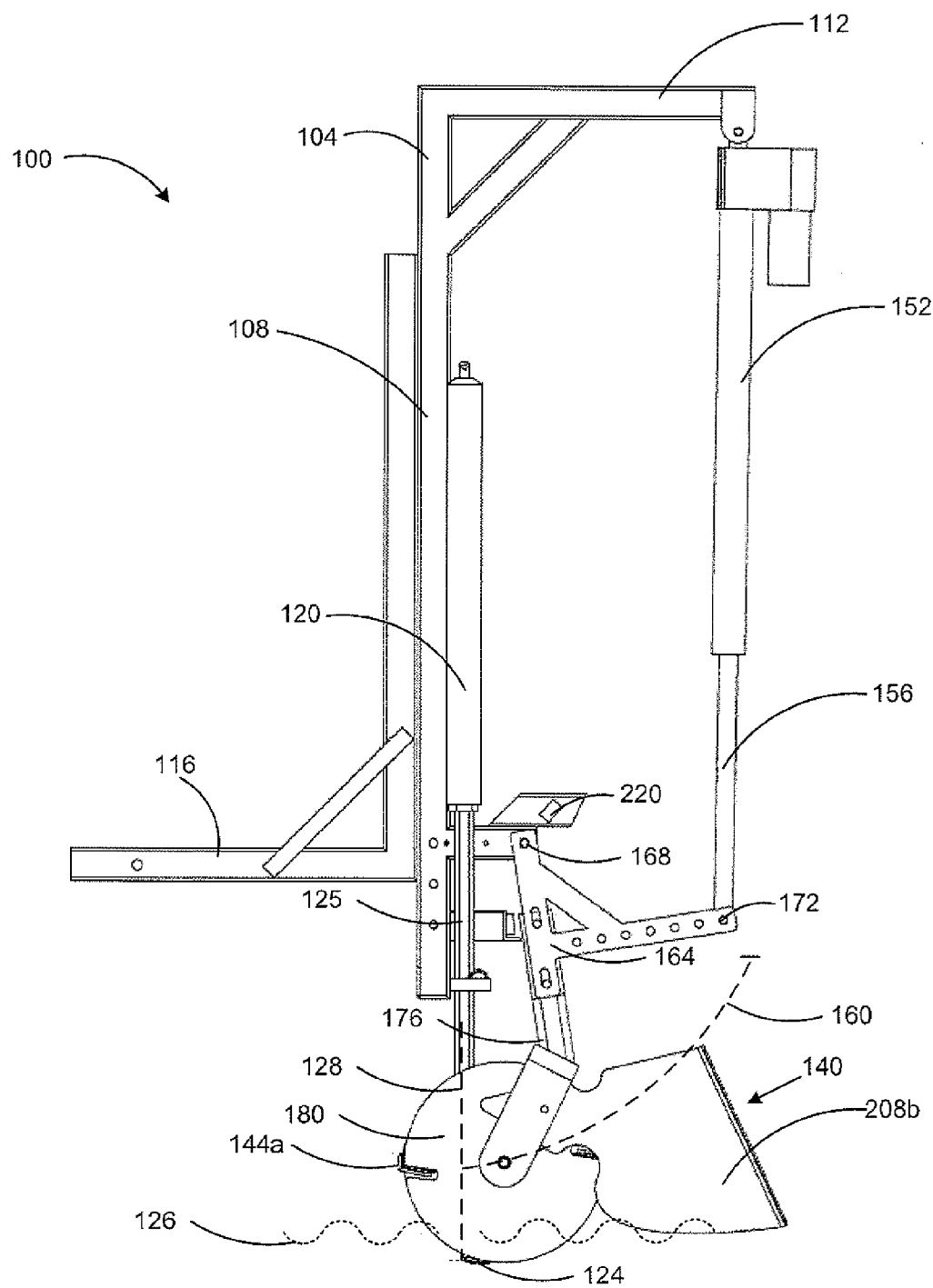
FIG. 11A is a side elevation view of the soil analysis apparatus of FIG. 1, showing the blade assembly in an excavation position, corresponding to a second sensor permitting configuration, and showing sensor(s) in the sensing position and projecting through the opening of the blade assembly.
Figure 11B:
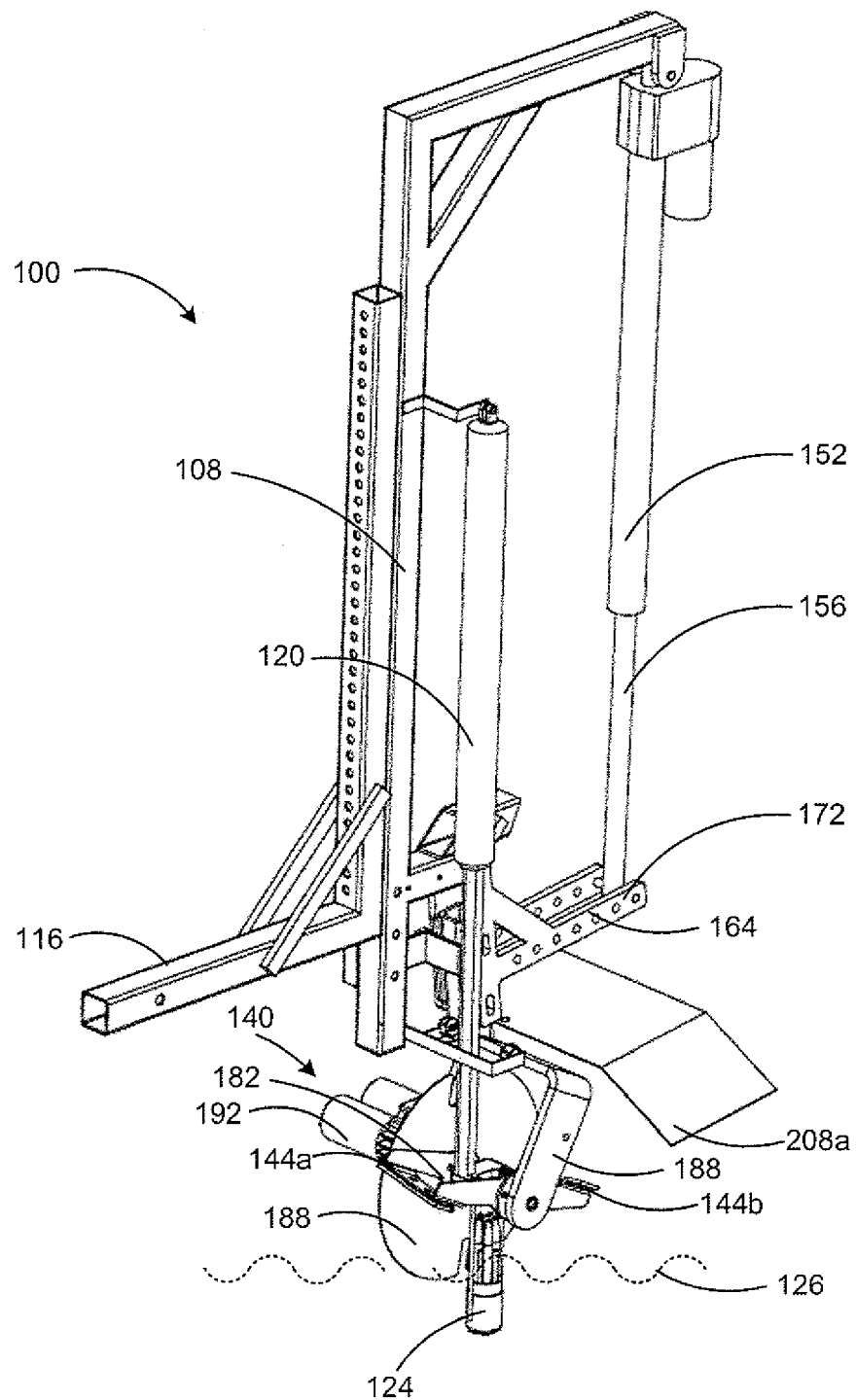
FIG. 11B is a perspective view of the soil analysis apparatus of FIG. 8, with one disk member not shown, showing the blade assembly in an excavation position corresponding to a second sensor permitting configuration, showing the additional guard member in an access position, and showing sensor(s) in the sensing position and projecting through the opening of blade assembly.
Figure 11C:
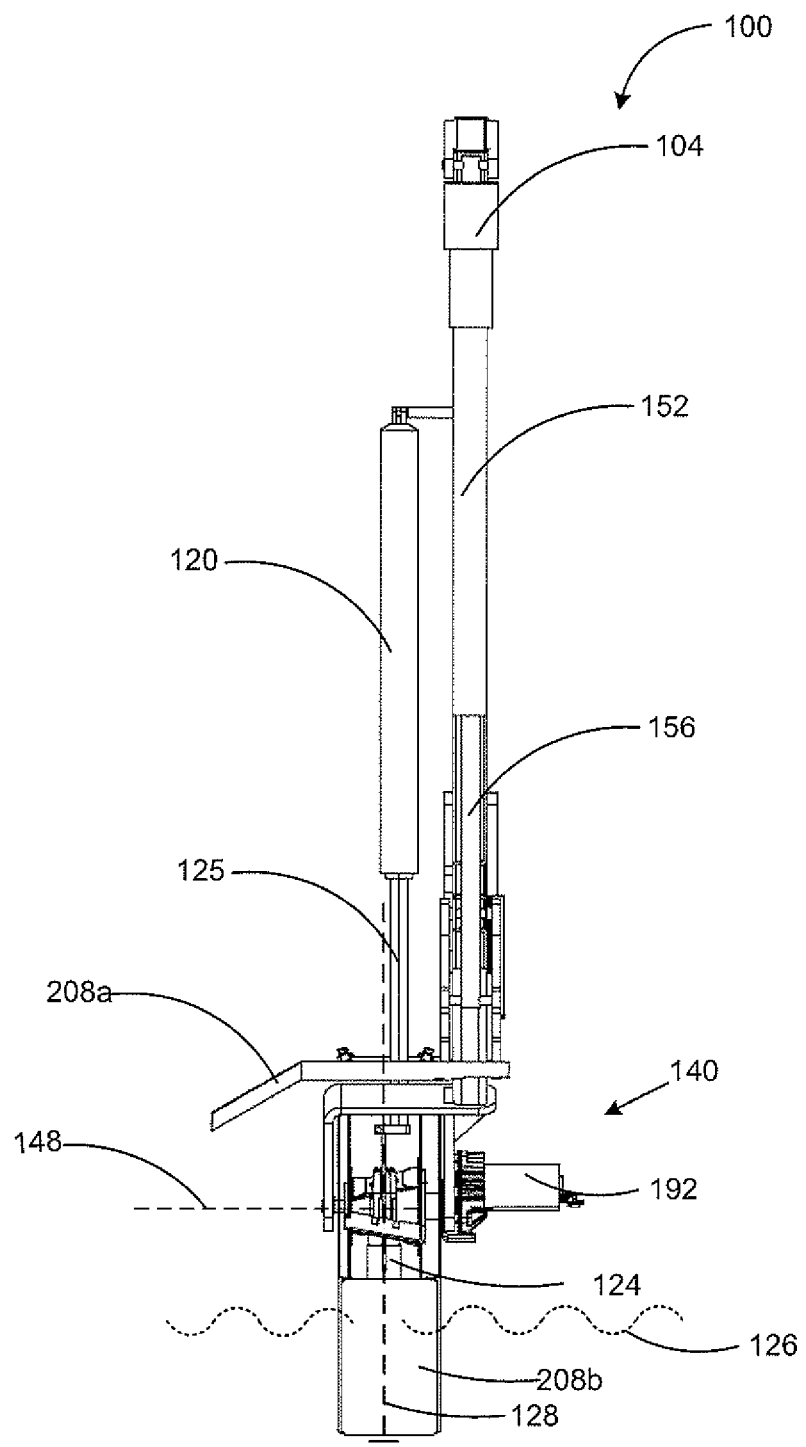
FIG. 11C is a rear elevation view of the soil analysis apparatus of FIG. 11B.
Figure 11D:
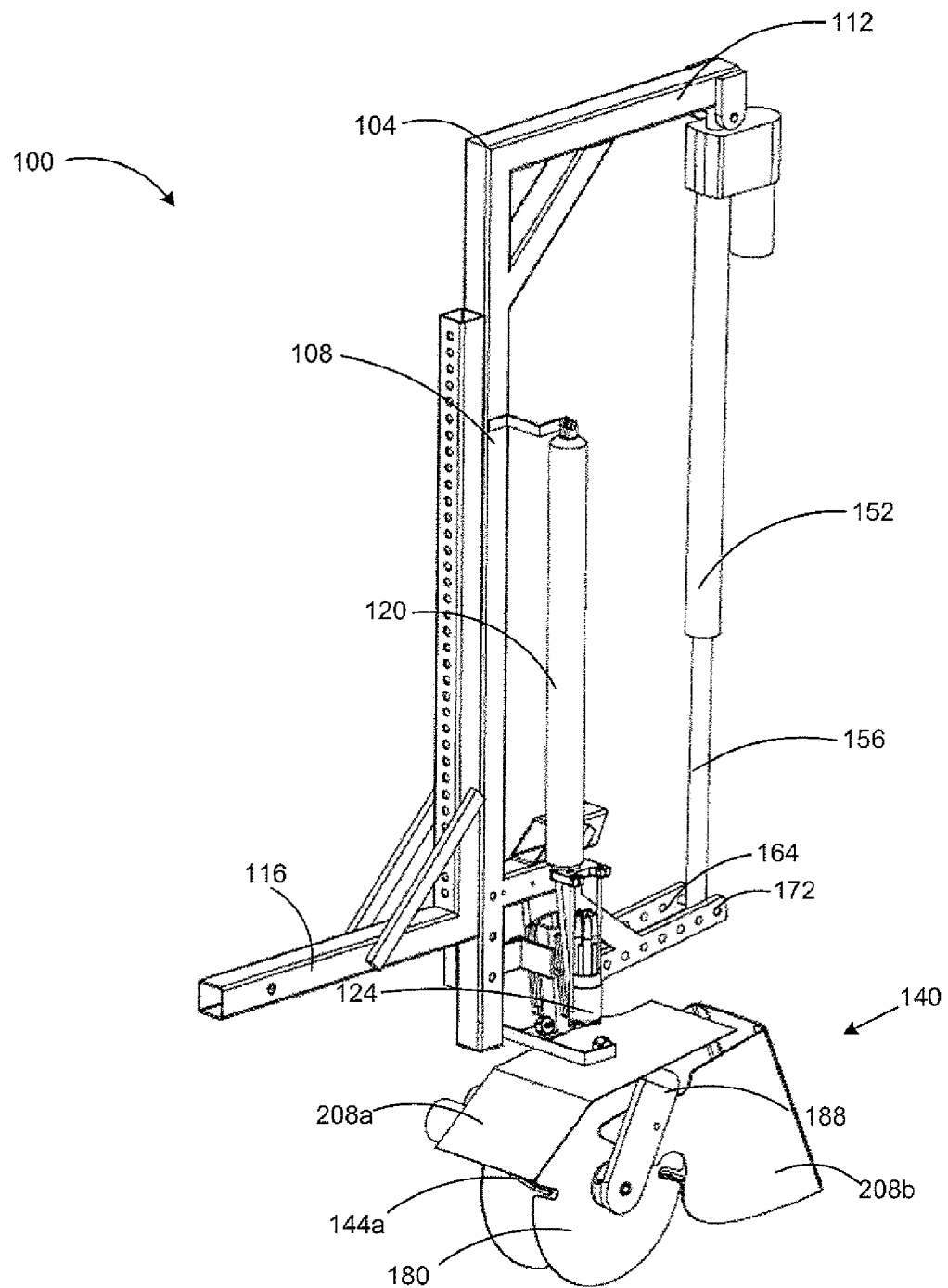
FIG. 11D is a perspective view of the soil analysis apparatus of FIG. 11C, showing the additional guard member in a guard position.

In some examples, the guard member 208a can be coupled to the soil analysis apparatus 100 so that when the at least one sensor element 124 is in the initial position, the guard member 208a is positioned substantially between the at least one sensor element 124 and the blade assembly 140 (as shown in FIG. 11D). The guard member 208a may occupy a space that intersects with the sensor displacement path 128. In this position, the guard member 208a substantially shields the at least one sensor element 124 from material being thrown up by the blade assembly 140 when excavating material from the soil surface 126.

In some examples, the guard member 208a can be displaced from a guard position, shown in FIG. 11D, to an access position, shown in FIGS. 11B, and 11C, wherein the guard member 208 is positioned remote of the sensor displacement path 128. For example, the guard member 208 may be pivotally or slidably attached to the frame 104 of the soil analysis apparatus 100. As the at least one sensor element 124 is displaced by the first actuator 120 along the sensor displacement path 128 from the initial position to the sensing position, a portion of the housing 204 may abut against the guard member 208a, causing the guard member 208a to move to the access position. In some examples, the guard member 208a can be biased to the guard position such that when the at least one sensor element 124 is displaced back to its initial position, the guard member 208a returns to the guard position.

Referring to FIG. 5, in the example shown, the soil analysis apparatus 100 further includes at least one jet nozzle 212 configured to spray a liquid onto the at least one sensor element 124. The spraying of a liquid from the at least one jet nozzle 212 may clean the at least one sensor element 124, which may have become dirtied following a soil sampling operation. In some examples (not shown), the at least one jet nozzle 212 may be positioned on a top side of the guard member 208a, and may be oriented towards the at least one sensor element 124 in the initial position. The at least one jet nozzle 212 may also be positioned at other suitable locations of the soil analysis apparatus 100 while still allowing for a liquid to be sprayed towards the at least one sensor element 124.

Referring still to FIG. 5, the soil analysis apparatus 100 further includes a first limit switch 216. The first limit switch 216 is located along the sensor displacement path 128 and is actuated when the at least one sensor element 124 reaches the initial position. Actuation of the first limit switch 216 breaks the circuit formed by the first actuator 120 with a power supply, thereby preventing further retracting of the rod portion 125 of the first actuator 120. Actuation of the first limit switch 216 can also be used as a signal indicating that the at least one sensor element 124 has reached the initial position.

In the example shown, the soil analysis apparatus 100 further includes a second limit switch 220. The second limit switch 220 is located so as to be actuated by one of the second actuator 152, blade assembly 140, or pivoting member 164 when the blade assembly 140 reaches the raised position. Actuation of the second limit switch 220 breaks the circuit formed by the second actuator 152 with a power supply, thereby preventing further retracting of the rod portion 156 of the second actuator 152. Actuation of the second limit switch 220 can also be used as a signal indicating that the blade assembly 140 has reached the raised position.

Figure 6A:
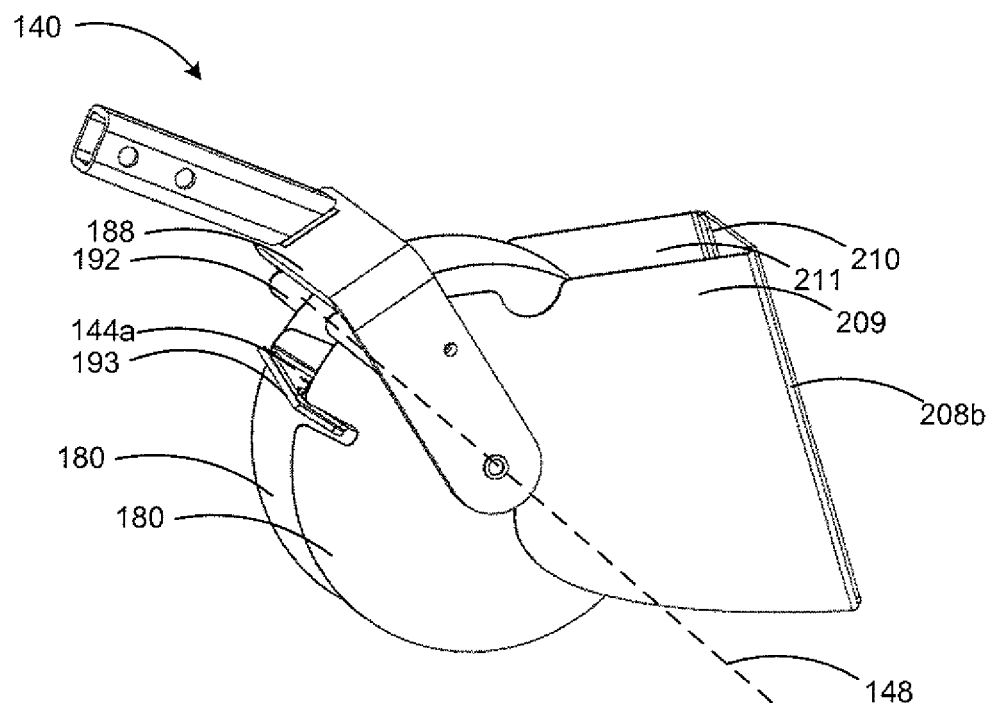
FIG. 6A is a perspective view of the blade assembly of FIG. 1, having an example guard member mounted thereto.

Referring now to FIG. 6A, a second example of a guard member 208 is shown. In this example, the guard member 208b is attached to the blade assembly 140. The guard member 208b includes opposing side walls 209 that are freely pivotally coupled to the support member 188. The opposing side walls 209 extend in a direction that corresponds to the direction in which soil material is projected as the blade assembly 140 removes the soil material from the soil surface 126. The opposing side walls 209 are joined by a rear wall 210 extending transversely between the opposing side walls 209. The opposing side walls 209 and the rear wall 210 define a collecting chamber 211. Since the guard member 208b is freely pivotally coupled to the support member 188, it will rest on the soil surface 126 under the force of gravity. As soil material is removed from the soil surface 126 as the blade assembly 140 is displaced from its soil excavating position to its excavation position, the removed soil material is collected within the collecting chamber 211. Furthermore, as the blade assembly 140 is displaced from its excavation position to its raised position, the guard member 208b continues to rest upon the soil surface 126 for a portion of the displacement, and the soil material of the collecting chamber 211 is returned to the soil surface 126 at the test location. The guard member 208b may further provide a shield behind the blade assembly 140 to protect users operating the soil analysis apparatus 100. In some examples, a stop (not shown) may be provided to limit downward pivoting of the guard member 208b when the blade assembly 140 is moved to the raised position.

Figure 6B:
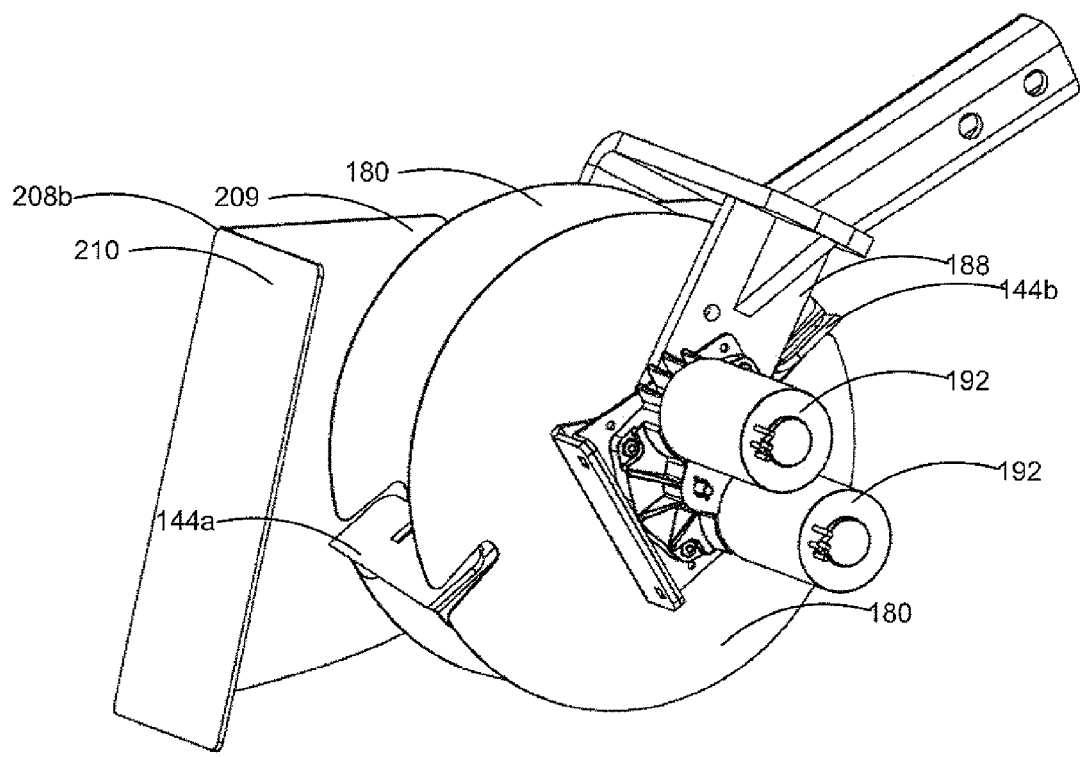
FIG. 6B is a perspective partial cut-away view of the blade assembly of FIG. 6A.

Referring now to FIG. 6B, in the example shown, two motors 192 are provided for rotating the blades 144a, 144b about the axis 148.

Figure 7:
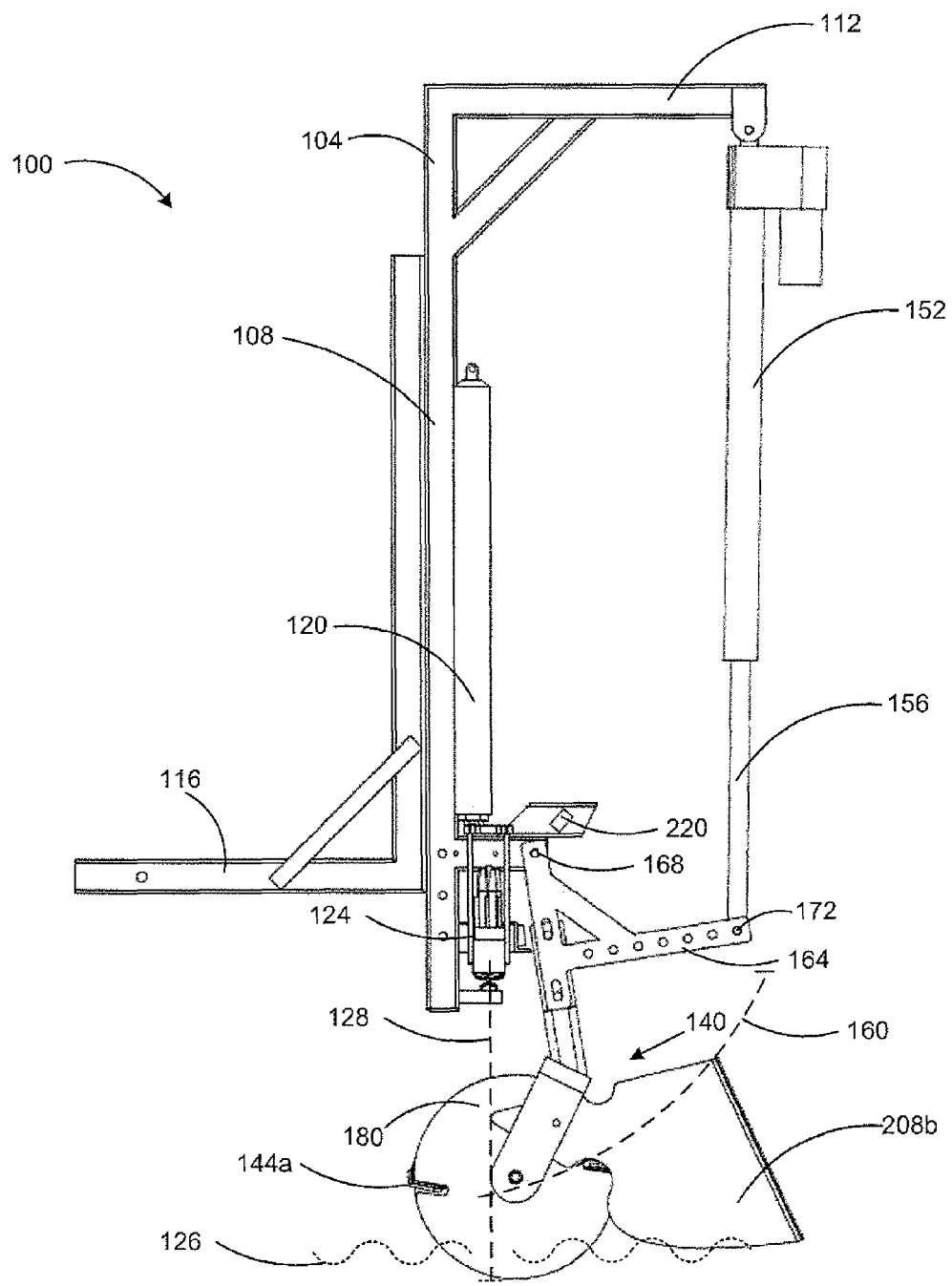
FIG. 7 is a side elevation view of the soil analysis apparatus of FIG. 1, showing the blade assembly in an excavation position.

Referring now to FIG. 7, therein illustrated is a side elevation view of the example soil analyzer apparatus 100, in which the blade assembly 140 has reached its excavation position. As illustrated, a portion of the blade assembly 140 is now located below the soil surface 126. Further, a portion of the blade assembly 140 is now intersecting the sensor displacement path 128. The bottom edge of the guard member 208 is also resting upon the soil surface 126. Accordingly, soil material has been removed at the test location and the test location has been prepared so as to be ready for analysis using the at least one sensor element 124.

Figure 8:
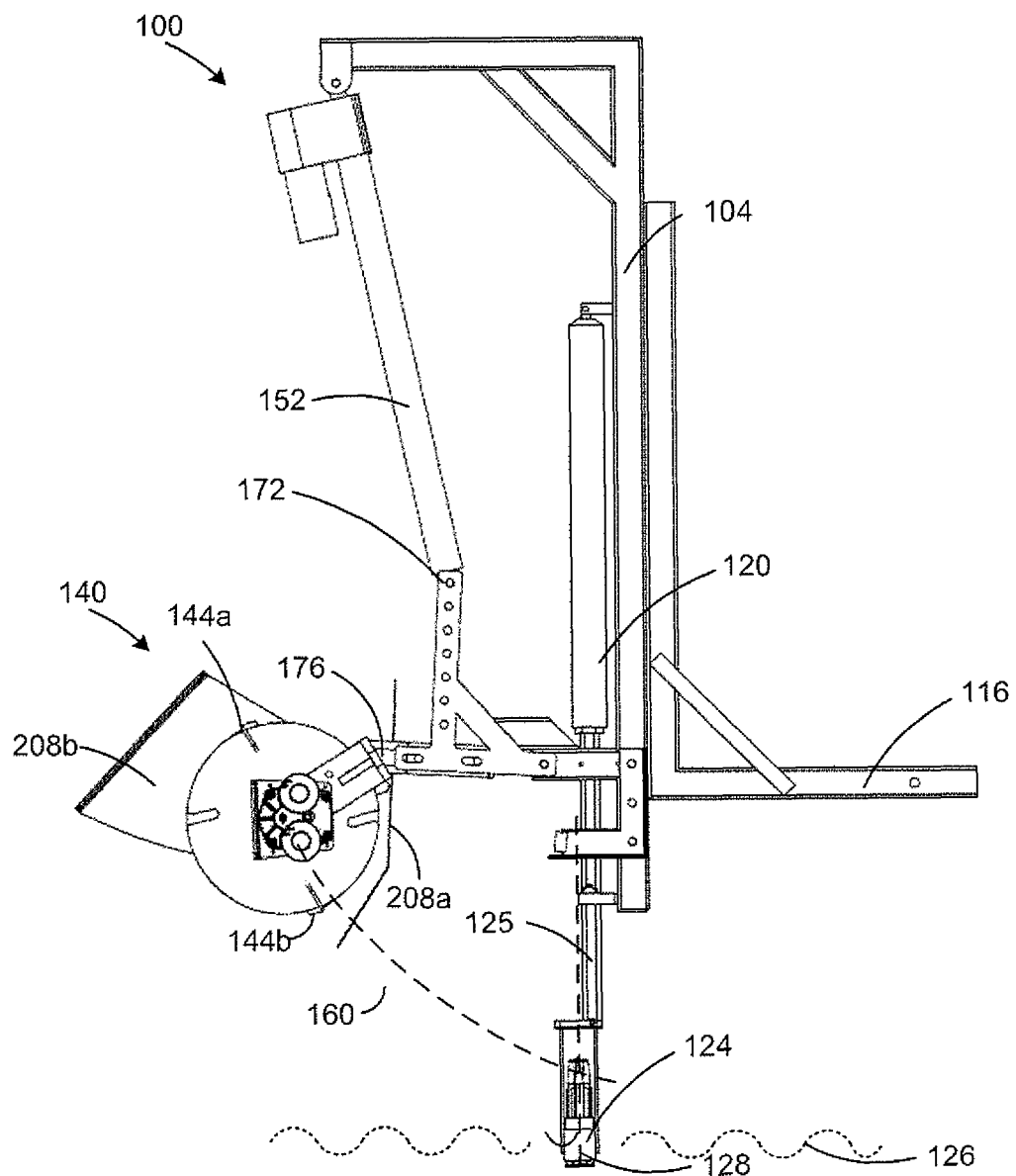
FIG. 8 is a side elevation view of an alternative soil analysis apparatus, which has an additional guard member, showing the blade assembly in a raised position that corresponds to a first sensor permitting configuration, and the sensor element in a sensing position.
Figure 9:
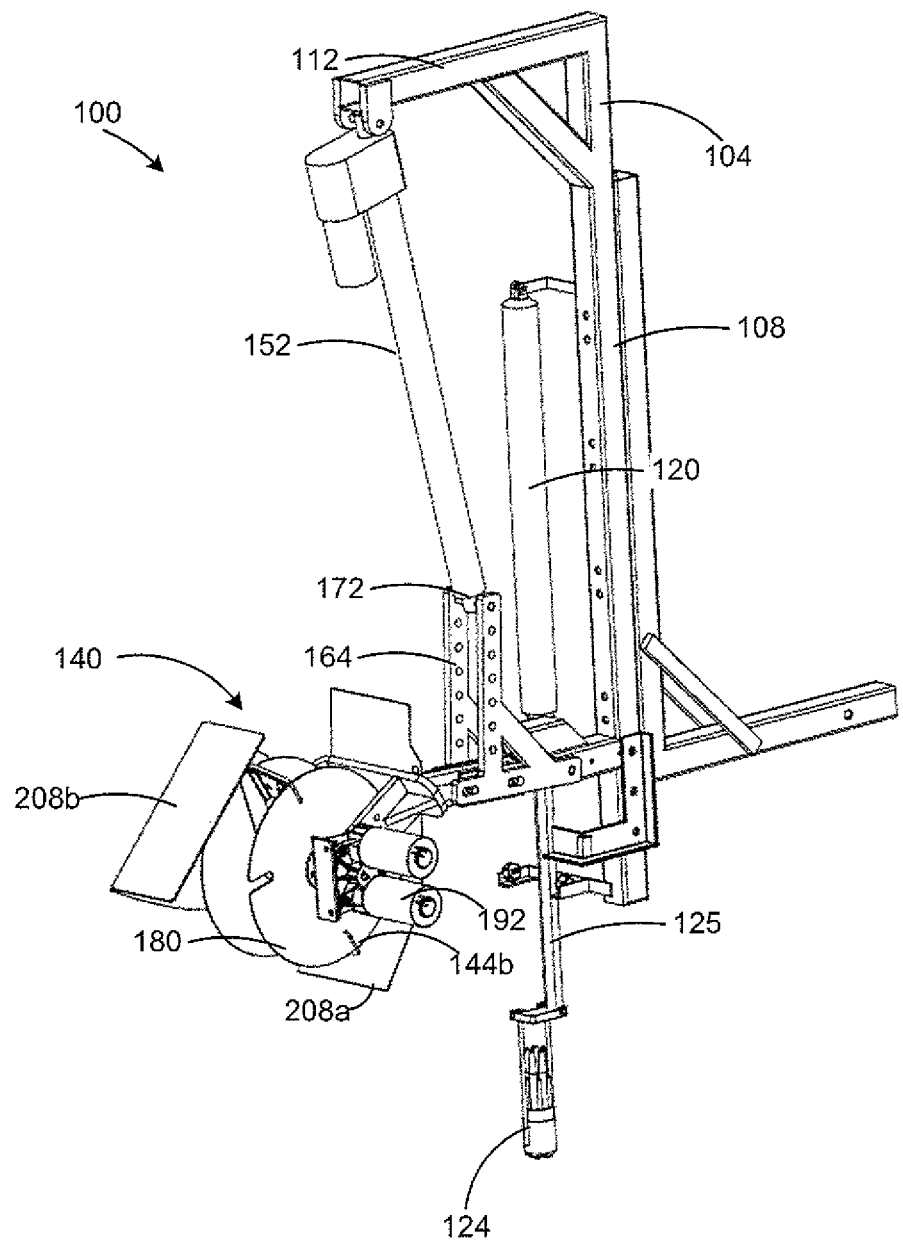
FIG. 9 is a perspective view of the soil analysis apparatus of FIG. 8.

The blade assembly 140 may have one or more sensor permitting configurations, in which the sensor element 124 may be moved to the sensing position without obstruction from the blade assembly 140. As will be described in further detail, a first sensor permitting configuration corresponds to the raised position, as shown in FIGS. 8 and 9. A second sensor permitting configuration corresponds to the excavation position, wherein the sensor element 124 may pass through the opening 182 of the blade assembly 140.

Referring now to FIGS. 8 and 9, the blade assembly 140 is illustrated when in its raised position, which is remote of the sensor displacement path 128, and corresponds to a first sensor permitting configuration of the blade assembly 140. In operation, the soil analysis apparatus 100 is positioned over a soil surface 126 of a test location and the blade assembly 140 is displaced from the raised position into an excavation position. Following an excavation operation, the at least one sensor element 124 is displaced along the sensor displacement path 128 to be positioned near the soil surface of the test location for sensing/measuring at least one property of the soil at the test location. This position corresponds to a sensing position of the at least one sensor element 124. If the blade assembly 140 is first displaced back to a position remote of the sensor displacement path 128, the at least one sensor element 124 can be displaced along the sensor displacement path 128 unobstructed.

Figure 10:
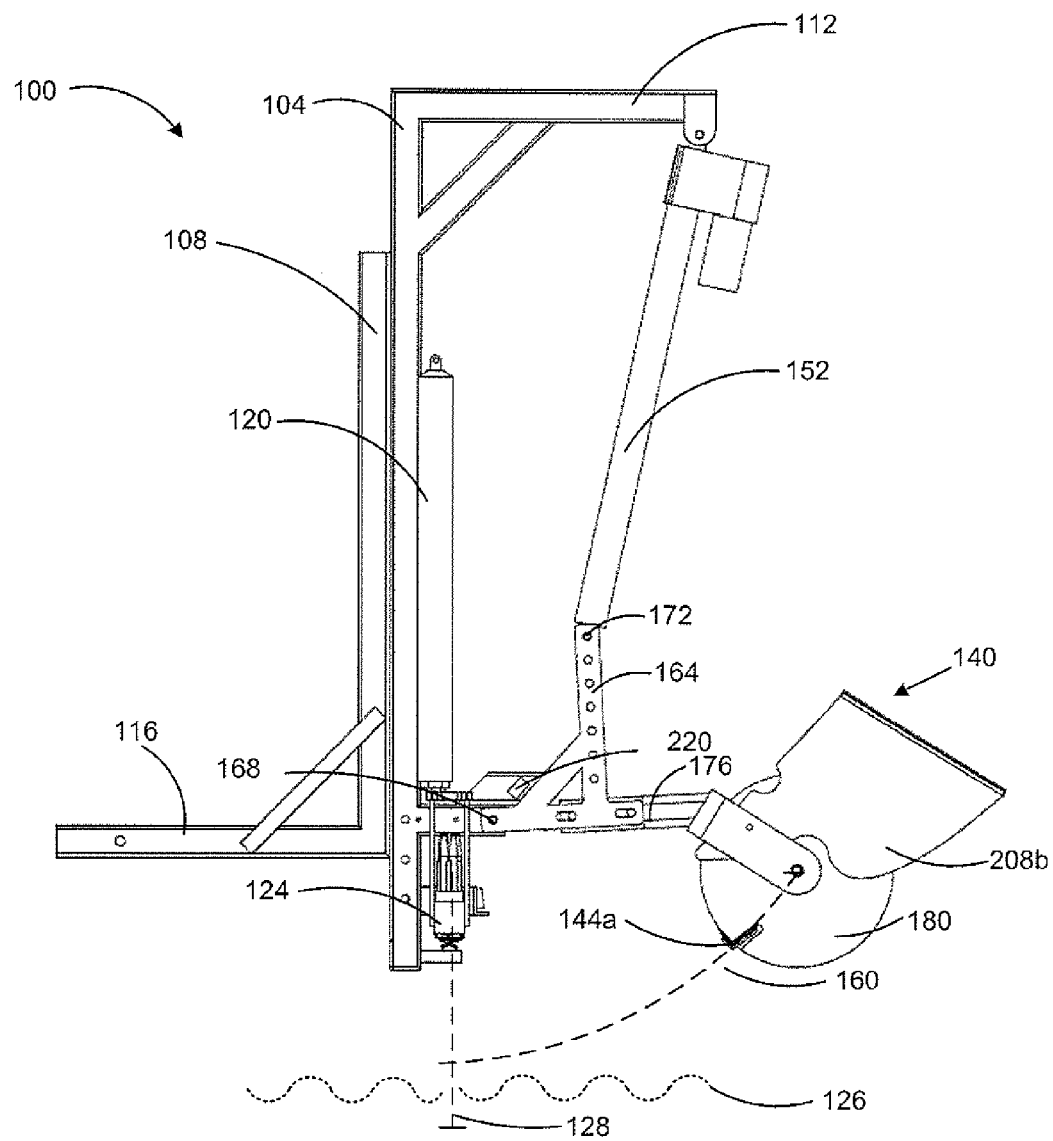
FIG. 10 is a side elevation view of the soil analysis apparatus of FIG. 1, in a transport position.

Referring now to FIG. 10 therein illustrated is a side elevation view of the example soil analysis apparatus in a transport position. As illustrated, the at least one sensor element 124 is displaced to its initial position and the blade assembly 140 is displaced to its raised position. Both the sensor element 124 and the blade assembly 140 are positioned at height spaced apart from the soil surface 126, which facilitates transportation and restricts damage to the sensor element 124 and blade assembly 140.

Referring now to FIGS. 11A, 11B, 11C, the second sensor permitting configuration is shown. The blade assembly 140 is illustrated as being in a position along the sensor displacement path 128, which corresponds to its excavation position. Following an excavation operation, the at least one rotatable blade of the blade assembly 140 is positioned in at least one predetermined rotational position such that the at least one sensor element 124 can be displaced through the interior opening 182 of the blade assembly 140. The combination of the blade assembly 140 being in the excavation position and the at least one rotatable blade being in the at least one predetermined rotational position corresponds to the second sensor permitting configuration of the blade assembly 140. The at least one predetermined rotational position can be any range of rotational positions allowing passage of the at least one sensor element 124 through the interior opening 182 of the blade assembly 140. The at least one sensor element 124 is then displaced along the sensor displacement path 128 to be positioned near the soil surface of the test location for sensing/measuring at least one property of the soil at the test location. This position corresponds to a sensing position of the at least one sensor element 124. When the blade assembly 140 is positioned such that the interior opening 182 of the blade assembly 140 is substantially aligned with the sensor displacement path 128, the at least one sensor element 124 can be displaced along the sensor displacement path 128 unobstructed to perform a sensing operation.

Figure 12:
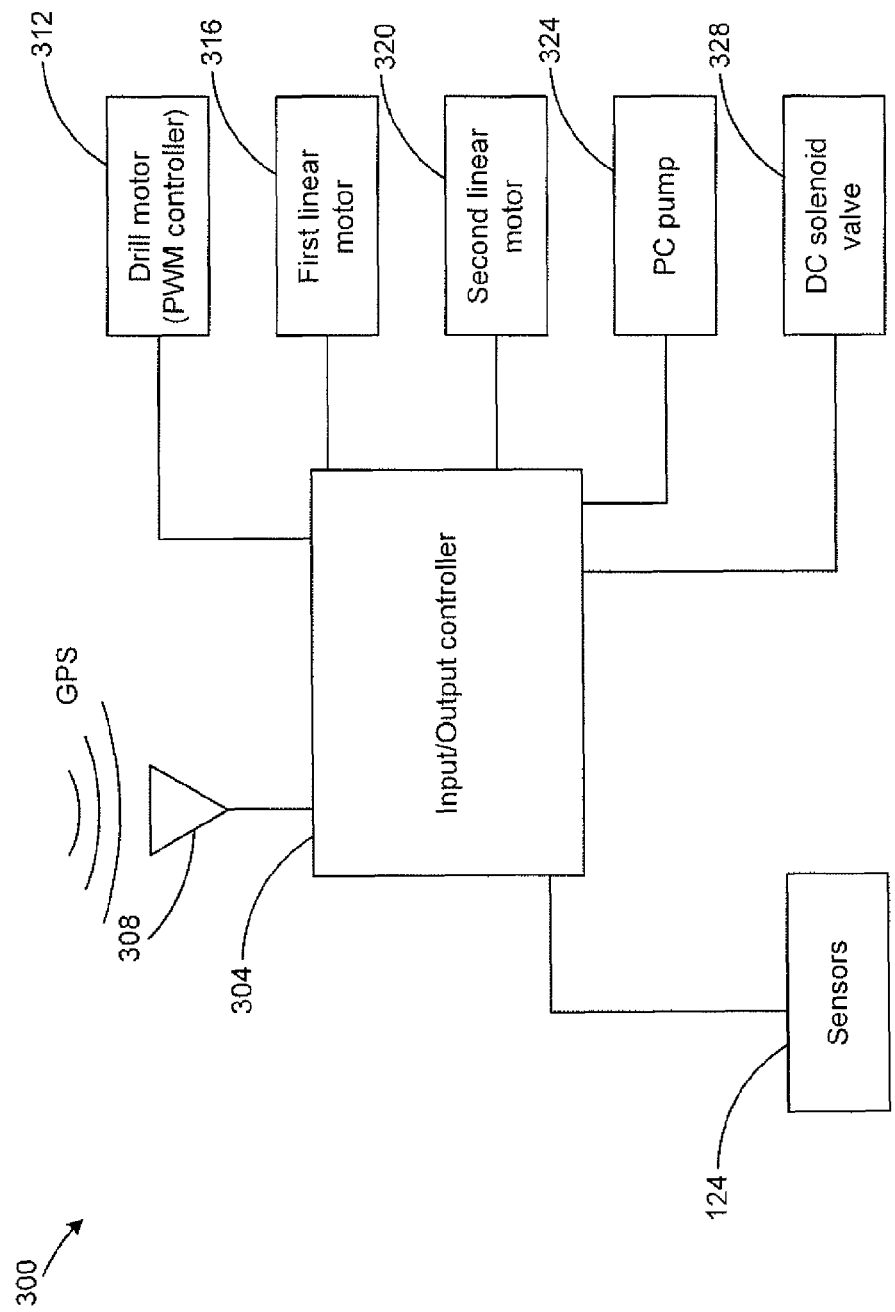
FIG. 12 is a schematic diagram of an example soil analysis system.

Referring now to FIG. 12, therein illustrated is a schematic diagram of the electronic components of a soil analysis system 300 according to one example. The soil analysis system 300 includes a controller 304 operable to receive input signals and output command signals. The controller 304 may be implemented in hardware or software, or a combination of both. In one example, the controller 304 is implemented on a programmable processing device, such as a microprocessor or microcontroller, Central Processing Unit (CPU), Digital Signal Processor (DSP), Field Programmable Gate Array (FPGA), general purpose processor, and the like. The programmable processing device is generally coupled to program memory or has its own program memory. The program memory may be used to store instructions used to program the controller 304 to perform various functions as described herein. The program memory can include non-transitory storage media, both volatile and non-volatile, including but not limited to, random access memory (RAM), dynamic random access memory (DRAM), static random access memory (SRAM), read-only memory (ROM), programmable read-only memory (PROM), erasable programmable read-only memory (EPROM), electrically erasable programmable read-only memory (EEPROM), flash memory, magnetic media, and optical media. In some examples, the microcontroller may be a PIC24 series microcontroller.

In some examples, the soil analysis system 300 further includes a GPS module 308 coupled to the controller 304. The controller 304 can receive geo-location data from the GPS module 308.

In some examples, the controller 304 is coupled to a drill motor 312, which may be the first motor 192 of the blade assembly 140 for rotating the at least one blade (FIG. 2), for example to a motor controller of the drill motor 312. The controller 304 may transmit a signal to the motor controller indicating a desired rotational speed. The motor controller may subsequently output appropriate modulated signals to the drill motor 312 for controlling the rotational speed of the drill motor 312. In some examples, the motor controller is a pulse-wave modulated (PWM) controller.

The controller 304 may further be coupled to a first linear motor 316. The actuation of the first linear motor 316 can be controlled by varying the value of a potentiometer of the first linear motor 316. The first linear motor 316 may form a part of the first actuator 120, to which is coupled the at least one sensor element 124. The first linear motor 316 may move the at least one sensor element 124 between the initial position and the sensing position by actuating the rod portion 125 of the first actuator 120.

The controller 304 may further be coupled to a second motor 320, which may be a linear motor. The actuation of the second motor 320 can be controlled by varying the value of a potentiometer of the second motor 320. The second motor 320 may form a part of the second actuator 152, to which is coupled the blade assembly 140. The second motor 320 may move the blade assembly 140 between the raised position and the excavation position by actuating the rod portion 156 of the second actuator 152.

The controller 304 may further be coupled to a pump 324. The pump 324 may provide for a liquid/solution from a reservoir to be moved to the at least one jet nozzle 212 of the soil analysis apparatus 100. The controller 304 may be operable to control the pump 324 so that the at least one jet nozzle 212 sprays liquid from the liquid reservoir.

The controller 304 may further be coupled to a valve 328. The controller 304 may be operable to control the valve 328 so that a nozzle deposits a liquid/solution onto the test location. The depositing or spraying of the liquid/solution may be useful for preconditioning the soil at the test location prior to sensing by the at least one sensor element 124. One or more of the drill motor 312, first motor 316, second motor 320, pump 324 and valve 328 may be connected to a relay driver, which may provide the required electrical power to drive the components.

The controller 304 may further be coupled to the at least one sensor element 124. The controller 304 may be operable to control the at least one sensor element 124 to measure/analyze a property of the soil. The soil analysis system 300 can be configured to carry out an automated soil analysis at a test location.

Figure 13:
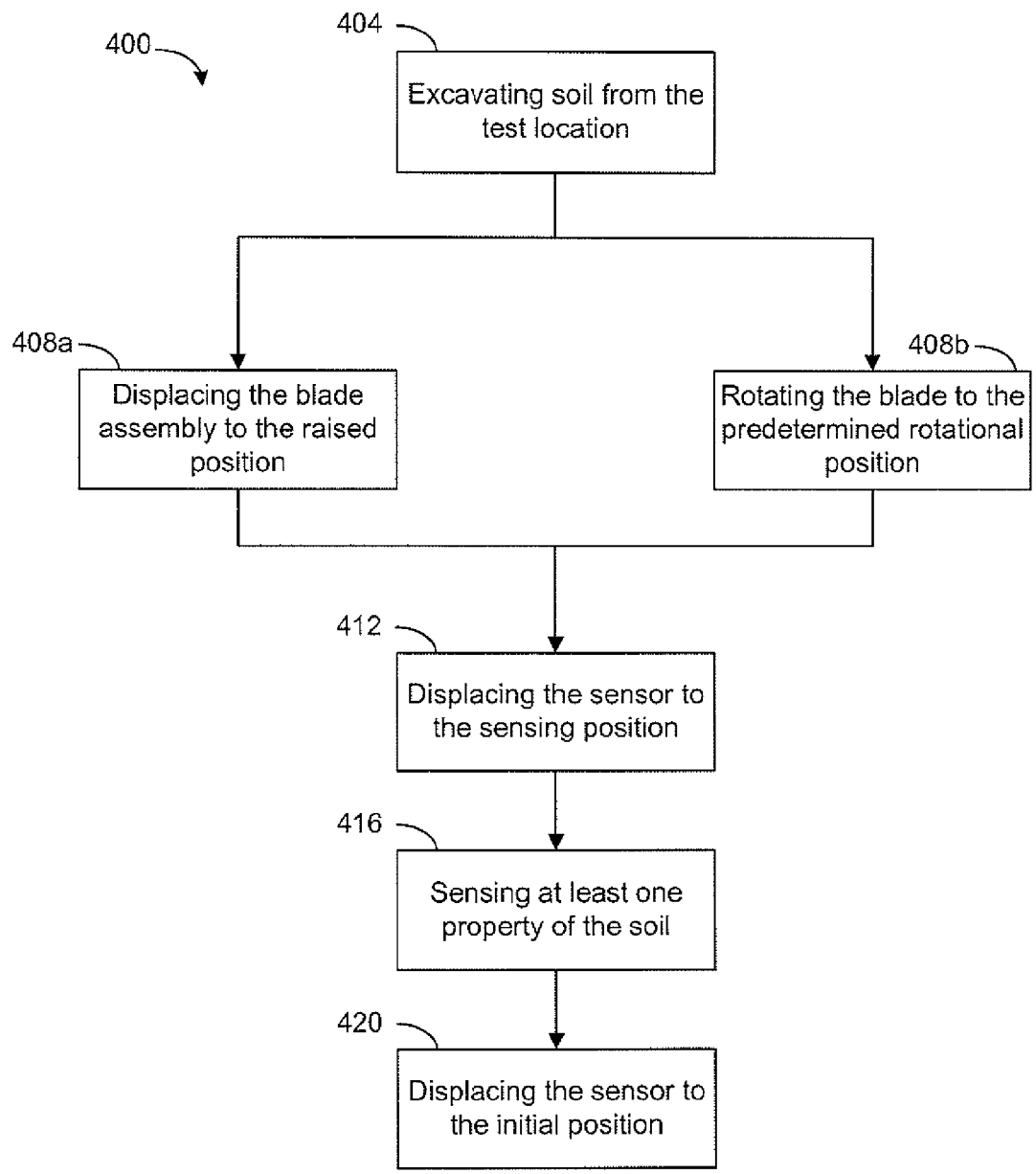
FIG. 13 is a schematic diagram of an example method for analyzing soil.

Referring now to FIG. 13, therein illustrated is a schematic diagram of an example method 400 for sampling soil at a test. Method 400 may be carried out by a series of commands inputted by a user, or may be carried out automatically through commands provided by an appropriately configured controller 304.

Step 404 is a soil excavation step. As described hereinabove, the excavation step 404 is typically performed by displacing the blade assembly 140 towards its excavation position and subsequently actuating the blade assembly 140 causing the at least one blade to rotate. The blade assembly 140 can be actuated while moving it to the excavation position.

At step 408a the blade assembly 140 is displaced away from the test location to the raised position, which in this example corresponds to the first sensor permitting configuration. In this position, the blade assembly is remote of the sensor displacement path 128. The sensor displacement path 128 is thus cleared such that the at least one sensor element 124 can be freely displaced from its initial position to the sensing position.

Alternatively, at step 408b, the at least one blade of the blade assembly 140 is rotated to a predetermined rotational position such that the interior opening 182 of the blade assembly 140 is aligned with the with the sensor displacement path 128. This corresponds to the second sensor permitting configuration. Accordingly, the sensor displacement path 128 is cleared of any obstructions and the at least one sensor element 124 can be freely displaced from its initial position to the sensing position through the interior opening 182.

Step 412 is a sensor displacement step in which the sensor element 124 is displaced from its initial position to the sensing position. Step 416 is a sensing step in which the at least one sensor element 124 measures/analyzes a property of the soil. At step 416, a solution may be injected/deposited onto the soil. In a further embodiment of the present disclosure, the solution may chemically react with at least one soil component to produce a reaction product that can be detected by the at least one sensor element 124.

At step 420 the at least one sensor element 124 is displaced back to its initial position. Step 420 may optionally include a step in which a jet of water or other cleaning solution is sprayed onto the at least one sensor element 124 following a soil sampling operation to clean the at least one sensor element 124.

The blade assembly 140 may subsequently be displaced back to its raised position, if not already in the raised position.

Figure 14:
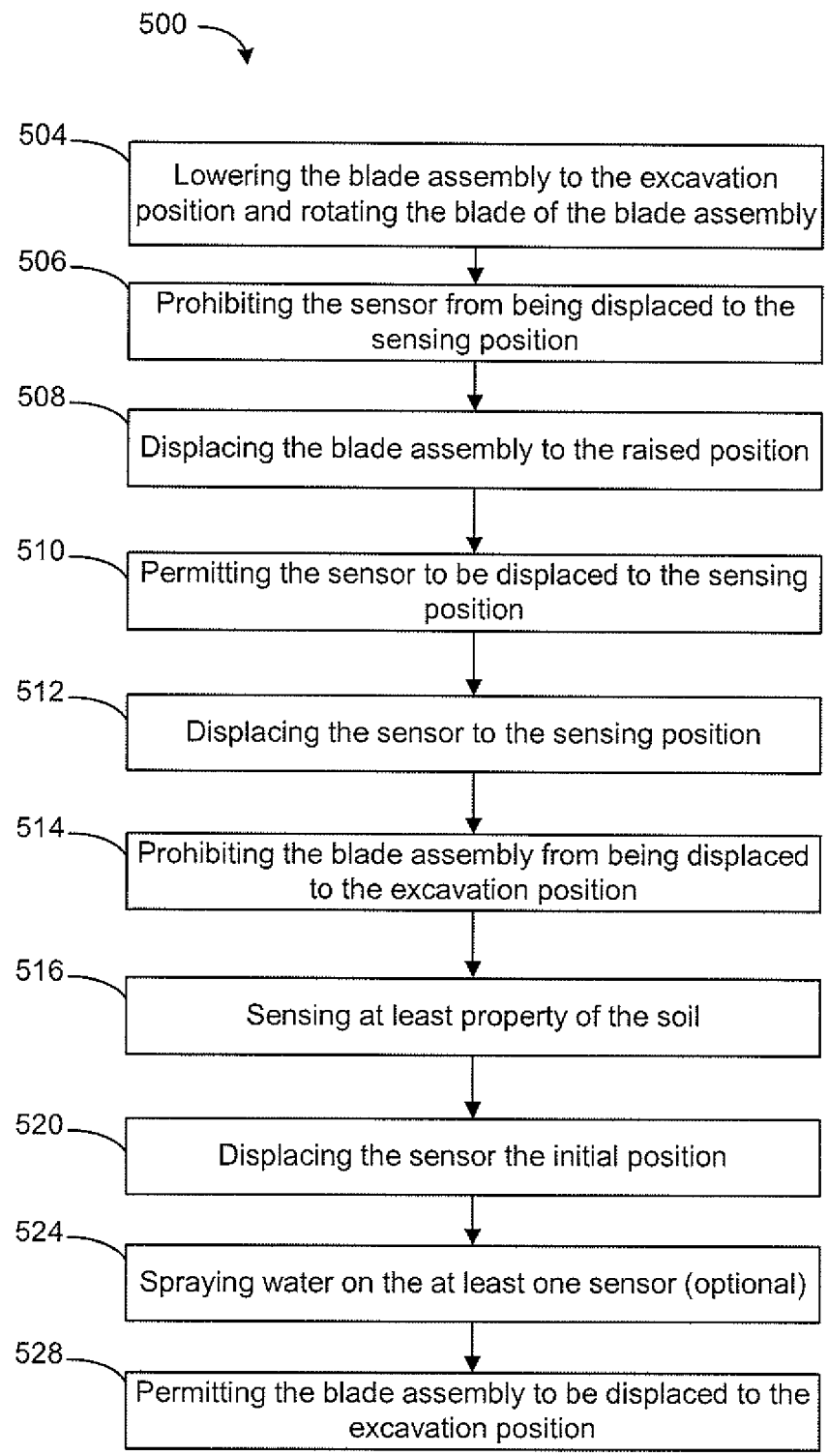
FIG. 14 is a schematic diagram of another example method for analyzing soil.

Referring now to FIG. 14, therein illustrated is a schematic diagram of an example method 500 for sampling soil at a test. In method 500, the function of the controller 304 during an automated soil analysis operation is further illustrated.

At step 504, the controller directs the second actuator 152 to lower the blade assembly 140 towards the excavation position and to subsequently actuate the blade assembly 140 causing the at least one blade to rotate. The blade assembly 140 can optionally be actuated while moving it to the excavation position.

At step 506, in response to the blade assembly 140 and the at least one blade being in a position that intersects with the sensor displacement path 128 (i.e. the blade assembly 140 and the at least one blade being in the excavation position), the controller 304 prohibits the first actuator 120 from displacing the at least one sensor element 124 into the sensing position. The controller 304 prevents the at least one sensor element 124 from contacting the blade assembly 140, thereby preventing damage to the soil analysis apparatus 100. When the controller 304 prohibits the first actuator 120 from displacing the at least one sensor element 124 to the sensing position, the system 300 may be non-responsive to external commands, such as user-inputted commands for displacing the at least one sensor element 124.

At step 508, the controller directs the second actuator 152 to displace the blade assembly 140 away from the excavation position towards the raised position, thus moving the blade assembly 140 away from the sensor displacement path 128. The sensor displacement path 128 is cleared of any obstruction by the blade assembly 140 and the at least one sensor element 124 can be freely displaced from the initial position to the sensing position.

At step 510, in response to the blade assembly 140 and the at least one blade being in a position remote from the sensor displacement path 128 (i.e. the blade assembly 140 and the at least one blade being in the raised position), the controller 304 permits the first actuator 120 to displace the at least one sensor element 124 to be lowered to the sensing position. The system 300 may become responsive to external commands, such as user-inputted commands, for displacing the at least one sensor element 124.

At step 512, the controller 304 directs the first actuator 120 to displace the at least one sensor element 124 to the sensing position, proximate the soil at the test location. The at least one sensor element 124 can be contacting the soil at the test location.

At step 514, in response to the at least one sensor element 124 being displaced to the sensing position, the controller 304 prohibits the second actuator 152 from displacing the blade assembly 140 to a position intersecting the sensor displacement path 128. The system 300 may thus be non-responsive to external commands, such as user-inputted commands for displacing the blade assembly 140 to the excavation position.

At step 516, the controller 304 directs the at least one sensor element 124 to measure/analyze a property of the soil at the test location. At step 516, a solution may be injected/deposited onto the soil. The solution may chemically reacts with at least one soil component to produce a reaction product that can be detected by the at least one sensor element 124.

At step 520, the controller 304 directs the first actuator 120 to displace the at least one sensor element 124 back to its initial position. Optionally, the controller 304 may be configured to direct at least one jet nozzle 212 to a spray a liquid (e.g. water) onto the at least one sensor element 124 in response to the at least one sensor element 124 being displaced back to the initial position (step 524).

At step 528, in response to the at least one sensor element 124 being displaced back to the initial position, the controller 304 directs the second actuator 152 to lower the blade assembly 140 towards a position intersecting the sensor displacement path 128, such as the excavation position. The system 300 may thus become responsive to external commands, such as user-inputted commands for displacing the blade assembly 140 to the excavation position.

Figure 15:
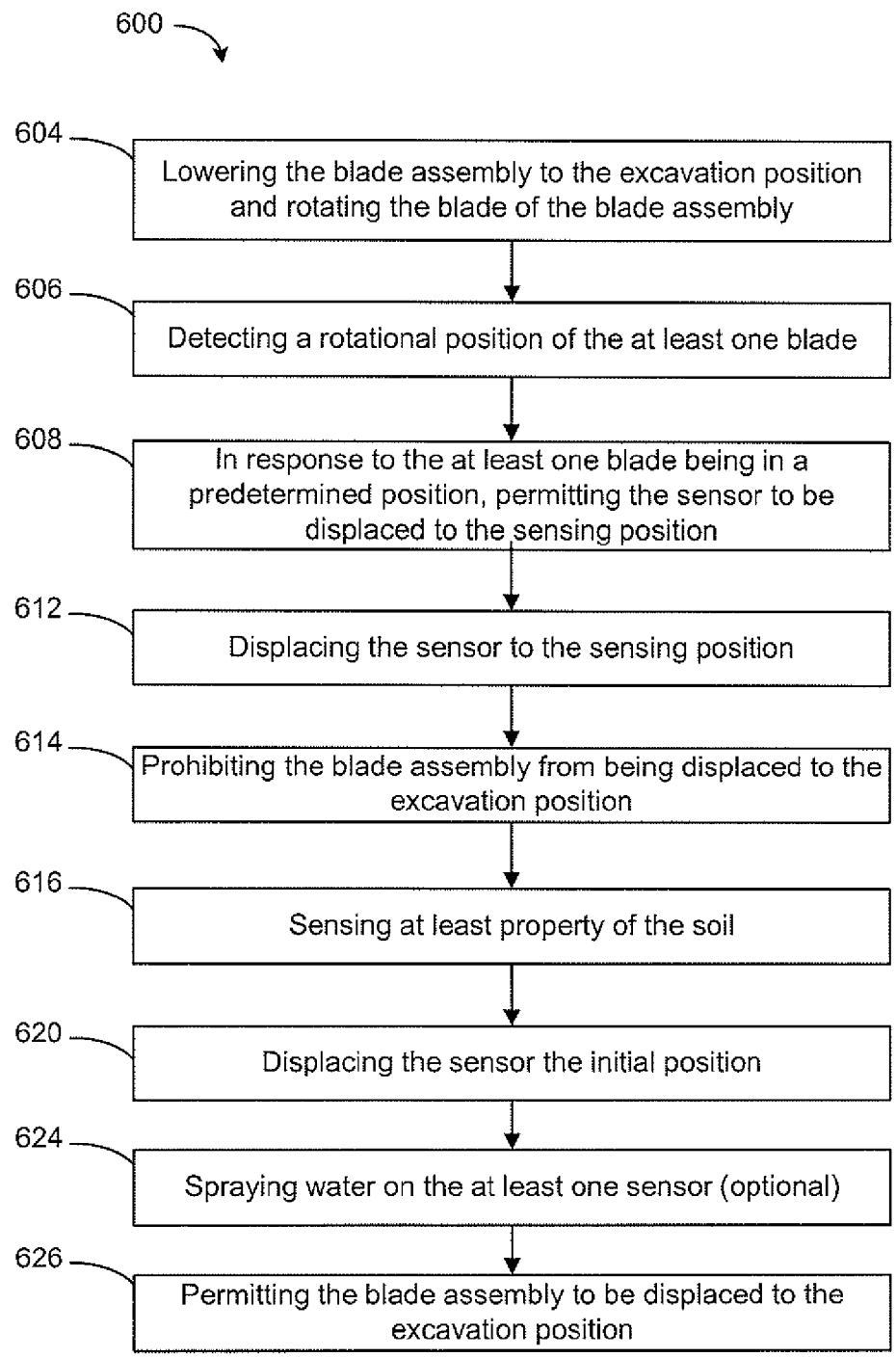
FIG. 15 is a schematic diagram of another example method for analyzing soil.

Referring now to FIG. 15, therein illustrated is a schematic diagram of another method 600 for sampling soil at a test location. In method 600, the function of the controller 304 during an automated soil analysis operation is further illustrated.

At step 604, the controller directs the second actuator 152 to lower the blade assembly 140 towards the excavation position and to subsequently actuate the blade assembly 140 causing the at least one blade to rotate. The blade assembly 140 can optionally be actuated while moving it to the excavation position.

At step 606, the controller 304 monitors the rotational position and speed of the at least one blade. The controller 304 may monitor whether the at least one blade of the blade assembly 140 is positioned in at least one predetermined rotational position such that the at least one sensor element 124 can be displaced through the interior opening 182 of the blade assembly 140. The controller 304 may further monitor whether the at least one blade is non-rotating. In some examples, after controlling the motor to rotate the at least one blade for a number of rotations sufficient to excavate the test location, the controller 304 directs the motor to come to a stop.

At step 608, in response to the blade assembly 140 and the at least one blade 144 being positioned in at least one predetermined rotational position wherein the interior opening 182 of the blade assembly 140 is aligned with sensor displacement path 128 and the at least one blade is non-rotating, the controller 304 directs the first actuator 120 to displace the at least one sensor element 124 to the sensing position. The system 300 may thus become responsive to external commands, such as user-inputted commands, for displacing the at least one sensor element 124.

At step 612, the controller 304 directs the first actuator 120 to displace the at least one sensor element 124 to the sensing position, proximate or in contact with the soil at the test location. The at least one sensor element 124 may displaced through the interior opening 182 of the blade assembly 140 to the sensing position.

At step 614, in response to the at least one sensor element 124 being displaced to the sensing position, the controller 304 prohibits the second actuator 152 from displacing the blade assembly 140 from the excavation position. Moreover, the controller 304 prohibits the motor from actuating the at least one blade. The controller 304 prevents the blade assembly 140 from contacting the at least one sensor element 124, thereby preventing damage to the soil analysis apparatus 100.

At step 616, the controller 304 directs the at least one sensor element 124 to measure/analyze a property of the soil at the test location. In some examples, at step 616, a solution is injected/deposited onto the soil. The solution may chemically react with at least one soil component to produce a reaction product that can be detected by the at least one sensor element 124.

At step 620, the controller 304 directs the first actuator 120 to displace the at least one sensor element 124 back to its initial position. Optionally, the controller 304 may be configured to direct at least one jet nozzle 212 to a spray a liquid (e.g. water) onto the at least one sensor element 124 in response to the at least one sensor element 124 being displaced back to the initial position (step 624).

At step 626, in response to the at least one sensor element 124 being displaced back to the initial position, the controller 304 directs the second actuator 152 to displace the blade assembly 140 to the raised position. The system 300 may thus become responsive to external commands, such as user-inputted commands for displacing the blade assembly 140 to the raised position. The controller 304 may be configured to automatically displace the blade assembly 140 to the raised position once the at least one sensor element 124 has been moved back to its initial position. Spraying the soil prior to a sensing operation may be optional, for example depending on a specific soil property being measured.

Figure 16:
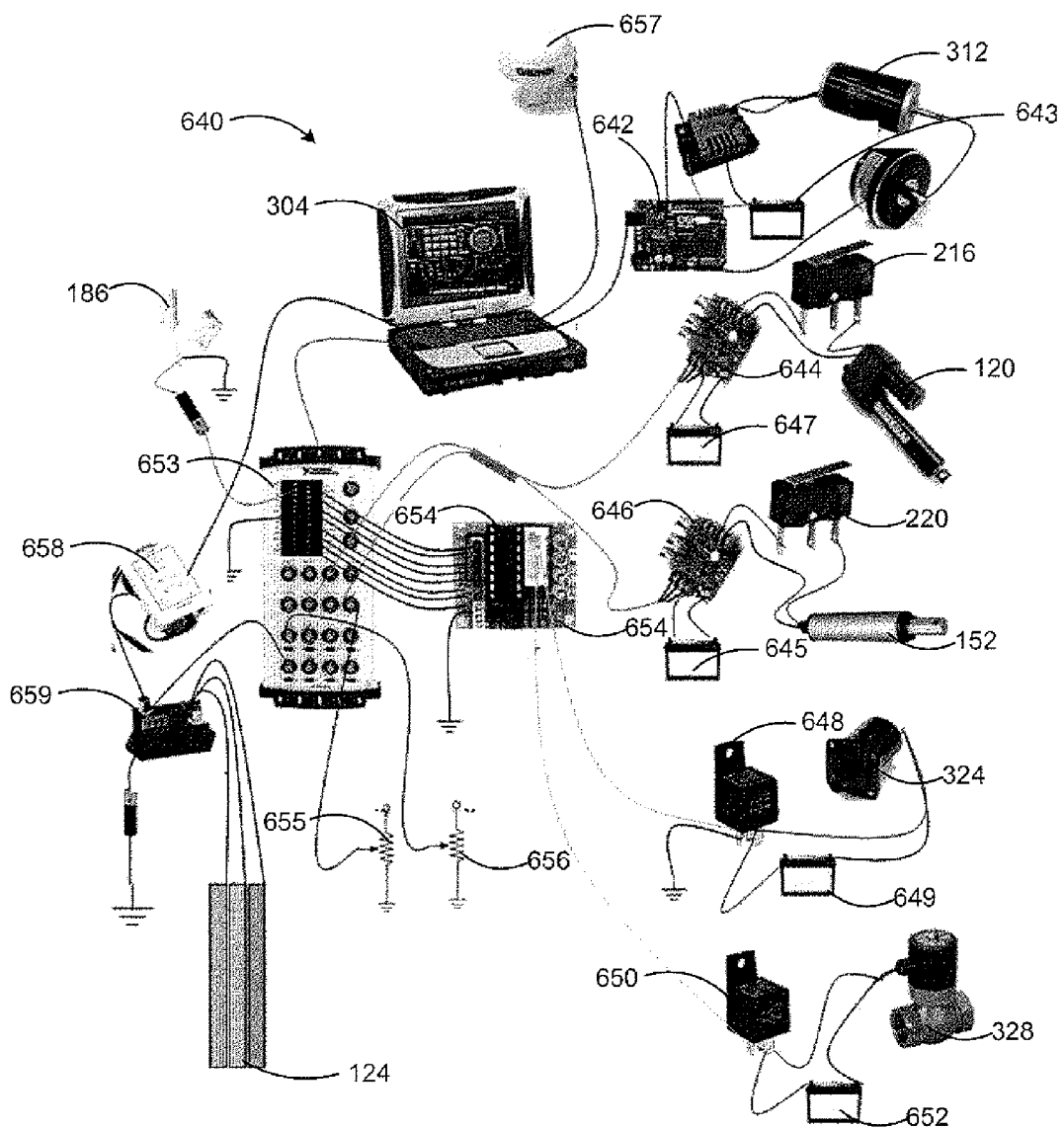
FIG. 16 is a detailed schematic diagram of an example soil analysis system.

Referring now to FIG. 16, therein illustrated is a detailed schematic diagram of the electronic components of an example soil analysis system 640 disclosure. The system includes the following components:

First linear actuator 120 (may also be first linear motor 316);
Sensor elements 124 ($H^+$, $K^+$, $NO_{3+}$ and/or $Na^+$ ion selective electrodes)
Second linear actuator 152 (may also be second linear motor 320)
Reed switch/potentiometer 186
First limit switch 216
Second limit switch 220
Controller 304
Drill motor 312
Pump 324
Valve 328
Drill motor controller (ex: PWM speed controller) 642
First battery (ex: 12 V battery) 643
First actuator controller (ex: PWM speed controller) 644
Second battery (ex: 12 V battery) 645
Second actuator controller (ex: PWM speed controller) 646
Third battery (ex: 12 V battery) 647
First DC relay for pump (ex: 12 V DC relay) 648
Fourth battery 649
Second DC relay (ex: 12 V DC relay) 650
Second DC relay for valve (ex: 12 V DC relay) 651
Fifth battery 652
Signal interface/interconnect (ex: USB interface) 653
Relay driver 654
Potentiometer of first linear actuator/linear motor 655
Potentiometer of second linear actuator/linear motor 656
GPS 657

Figure 17:
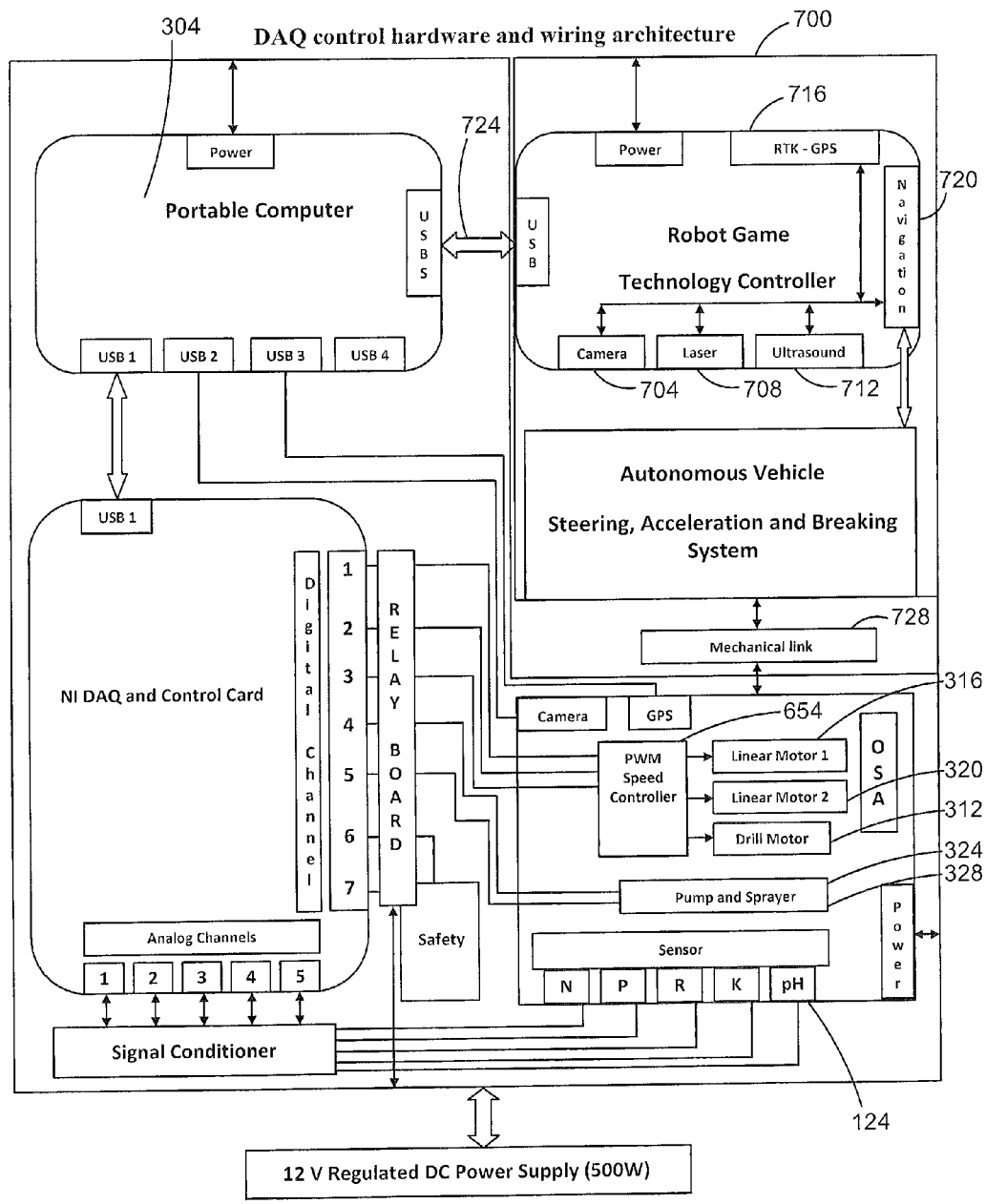
FIG. 17 is a schematic diagram of an example soil analysis system and autonomous vehicle system.

Referring now to FIG. 17, therein illustrated is a detailed schematic diagram of an example soil analysis system having autonomous navigation. In this example, the soil analysis apparatus 100 and soil analysis system 300 are joined with an autonomous vehicle 700. The autonomous vehicle 700 includes a navigation controller having one or more of a camera 704, laser guidance system 708, ultrasound guidance system 712, GPS guidance system 716 and map database 720. The autonomous vehicle 700 may be in electronic communication with the soil analysis system 300 through a first electronic coupling 724. The autonomous vehicle 700 may be mechanically linked to the soil analysis system 300 through a mechanical link 728. The mechanical link 728 may be the hitch of frame 104.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

The invention claimed is:

1. A soil analysis apparatus comprising:
    at least one sensor element for measuring a property of soil;
    a blade assembly having at least one blade and being displaceable between a raised position and an excavation position, the at least one blade being operable to excavate the soil at a test location when the blade assembly is in the excavation position, the blade assembly being further operable to enter a sensor permitting configuration; and
    a first actuator operable to displace the at least one sensor element from an initial position to a sensing position along a sensor displacement path when the blade assembly is in the sensor permitting configuration, the sensor element being proximate the soil at the test location when in the sensing position.

2. The soil analysis apparatus of claim 1, wherein the blade assembly comprises an interior opening and wherein when in the sensor permitting configuration the at least one blade is in a predetermined rotational position whereby the interior opening is substantially aligned with the sensor displacement path to permit displacement of the at least one sensor element through the interior opening to the sensing position along the sensor displacement path.

3. The soil analysis apparatus of claim 2, further comprising a detector for detecting when the at least one blade is in the predetermined rotational position.

4. The soil analysis apparatus of claim 3, wherein the detector comprises a potentiometer for determining a rotational position of the at least one blade.

5. The soil analysis apparatus of claim 2, wherein the blade assembly comprises:
    two opposing circular discs being spaced apart from each other and having aligned centers defining an axis of rotation; and
    two opposed blades coupled to circumferential portions of the discs, the excavating edge of each blade being oriented radially to the discs and away from each other; and
    wherein the two opposed circular discs and the two opposed blades define the interior opening.

6. The soil analysis apparatus of claim 2, further comprising:
    a motor mounted on the blade assembly for rotating the at least one blade;
    a second actuator for displacing the motor and the blade assembly;
    a detector for detecting the predetermined rotational position of the at least one blade;
    a controller for controlling the motor, the first actuator and the second actuator, the controller being configured to:
        receive a signal from the detector when the at least one blade is in the predetermined rotational position;
        permit the first actuator to displace the at least one sensor element to the sensing position in response to receiving the signal from the detector indicating that the at least one blade is in the predetermined rotational position.

7. The soil analysis apparatus of claim 6, wherein the controller is further configured to displace the at least one sensor element from its initial position to its sensing position in response to the second actuator displacing the at least one blade to a position intersecting the sensor displacement path and the at least one blade being in the predetermined rotational position, thereby displacing the at least one sensor element through the interior opening substantially aligned with the sensor displacement path.

8. The soil analysis apparatus of claim 7, wherein the controller is further configured to displace the at least one blade to a position remote of the sensor displacement path in response to the first actuator displacing the at least one sensor from the sensing position to the initial position.

9. The soil analysis apparatus of claim 1, wherein when in the sensor permitting configuration the blade assembly is in the raised position and is remote of the sensor displacement path, thereby permitting displacement of the at least one sensor to the sensing position along the sensor displacement path.

10. The soil analysis apparatus of claim 1, further comprising a second actuator coupled to the blade assembly, the second actuator operable to displace the blade assembly from the raised position to the excavation position, wherein in the excavation position the blade assembly occupies a portion of the sensor displacement path and in the raised position the blade assembly is remote of the sensor displacement path.

11. The soil analysis apparatus of claim 1, wherein the blade assembly comprises at least one circular disc rotatable about its center, the at least one blade being coupled to a circumferential portion of the disc and an excavating edge of the blade being oriented radially to the disc.

12. The soil analysis apparatus of claim 11, further comprising at least one motor for rotating the at least one blade of the blade assembly.

13. The soil analysis apparatus of claim 1, further comprising at least one jet nozzle for spraying a liquid on the at least one sensor element.

14. The soil analysis apparatus of claim 1, further comprising at least one nozzle for depositing a solution on the soil.

15. The soil analysis apparatus of claim 1, further comprising a guard member pivotally coupled to the blade assembly and operable to collect soil material excavated by the blade assembly from the test location and to return the collected soil material to the test location.

16. The soil analysis apparatus of claim 15, wherein the guard member comprises opposing side walls pivotally coupled to the blade assembly and a transverse wall extending between the opposing side walls, the opposing side walls and the transverse wall defining a collecting chamber for storing the collected soil material.

17. The soil analysis apparatus of claim 1, further comprising:
    a motor mounted on the blade assembly for rotating the at least one blade;
    a second actuator for displacing the motor and the blade assembly;
    a controller for controlling the motor, the first actuator and the second actuator, the controller being configured to:
        permit the first actuator to displace the at least one sensor element to the sensing position in response to the at least one blade being in a position remote of the sensor displacement path; and
        prohibit the first actuator from displacing the at least one sensor element to the sensing position in response to the at least one blade being in a position intersecting the sensor displacement path.

18. The soil analysis apparatus of claim 17, wherein the controller is further configured to prohibit the second actuator from displacing the at least one blade to a position intersecting the sensor displacement path when the sensor element is in the sensing position.

19. The soil analysis apparatus of claim 18, wherein the controller is further configured to permit the second actuator to displace the at least one blade to a position intersecting the sensor displacement path when the sensor element is in the initial position.

20. The soil analysis apparatus of claim 17, further comprising a frame and a pivoting member pivotally mounted to the frame;
    wherein the first actuator is coupled to the frame; and
    wherein the pivoting member is coupled to the second actuator and coupled to the blade assembly and wherein actuating the second actuator results in a pivoting movement of the pivoting member and pivotal displacement of the blade assembly.

21. A method for sensing or measuring at least one soil property at a test location, the method comprising:
    displacing a blade assembly and rotating at least one blade of the blade assembly to excavate soil material at the test location;
    displacing the blade assembly to a raised position away from the test location;
    displacing at least one sensor element into a sensing position; and
    sensing or measuring at least one soil property at the test location.

22. A method for sensing or measuring at least one soil property at a test location, the method comprising:

displacing a blade assembly and rotating at least one blade of the blade assembly to excavate soil material at the test location;

detecting a predetermined rotational position of the at least one blade;

displacing at least one sensor element into a sensing position along a sensor displacement path; and sensing or measuring at least one soil property at the test location.

23. The method of claim 22, wherein displacing the at least one sensor element comprises moving the at least one sensor element through an interior opening of the blade assembly substantially aligned with the sensor displacement path.

* * * * *